(12) United States Patent
Giffrida

(10) Patent No.: US 9,282,928 B1
(45) Date of Patent: *Mar. 15, 2016

(54) PARKINSON'S DISEASE DRUG OR MEDICATION, TITRATION, DELIVERY SYSTEM, AND METHOD

(71) Applicant: Joseph Giffrida, Hinckley, OH (US)

(72) Inventor: Joseph Giffrida, Hinckley, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 253 days.

This patent is subject to a terminal disclaimer.

(21) Appl. No.: 14/169,619

(22) Filed: Jan. 31, 2014

Related U.S. Application Data

(63) Continuation of application No. 13/455,423, filed on Apr. 25, 2012, now Pat. No. 8,679,038, which is a continuation of application No. 11/082,668, filed on Mar. 17, 2005, now Pat. No. 8,187,209.

(51) Int. Cl.
*A61B 5/00* (2006.01)
*A61B 5/11* (2006.01)

(52) U.S. Cl.
CPC ............ *A61B 5/4839* (2013.01); *A61B 5/1101* (2013.01); *A61B 5/4082* (2013.01)

(58) Field of Classification Search
CPC ...... A61B 5/11; A61B 5/1101; A61B 5/1124; A61B 5/103; A61B 5/4082; A61B 5/4839
See application file for complete search history.

*Primary Examiner* — Max Hindenburg
(74) *Attorney, Agent, or Firm* — Brian Kolkowski

(57) ABSTRACT

The present invention relates to a movement disorder monitor, and a method of measuring the severity of a subject's movement disorder. The present invention additionally relates to a drug delivery system for dosing a subject in response to the increased severity of a subject's symptoms. The present invention provides for a system and method, which can accurately quantify symptoms of movements disorders, accurately quantifies symptoms utilizing both kinetic information and electromyography (EMG) data, that can be worn continuously to provide continuous information to be analyzed as needed by the clinician, that can provide analysis in real-time, that allows for home monitoring of symptoms in subject's with these movement disorders to capture the complex fluctuation patterns of the disease over the course of days, weeks or months, that maximizes subject safety, and that provides remote access to the clinician or physician.

20 Claims, 24 Drawing Sheets

PARKINSON'S DISEASE DRUG OR MEDICATION, TITRATION, DELIVERY SYSTEM, AND METHOD

CROSS-REFERENCE TO RELATED APPLICATIONS

This application is a continuation of co-pending U.S. patent application Ser. No. 13/455,423, filed on Apr. 25, 2012, which was a continuation of the U.S. patent application Ser. No. 11/082,668, filed Mar. 17, 2005, and which issued as U.S. Pat. No. 8,187,209 on May 29, 2012.

The U.S. Government has a paid-up license in this invention and the right in limited circumstances to require the patent owner to license others on reasonable terms provided for by the terms of grant numbers 1 R43 NS043816-01A1 and 2R44NS043816-02/03 awarded by the National Institutes of Health.

BACKGROUND OF THE INVENTION

1. Field of the Invention

The present invention relates to a movement disorder monitor, and a method of measuring the severity of a subject's movement disorder. The present invention additionally relates to a drug delivery system for dosing a subject in response to changes in severity of a subject's symptoms.

2. Technical Background

Movement disorders include Parkinson's disease (PD) and essential tremor. The treatments can involve pharmaceutical interventions, fetal cell transplants, surgery, or deep brain stimulation in some of these disorders. The efficacy of these interventions is often judged by the interventions ability to alleviate patient symptoms and improve their quality of life. With Parkinson's disease for example, the major symptoms that affect quality of life are tremor, bradykinesia, rigidity, and dyskinesia. These symptoms are partly responsible for the subject's functional disability and social embarrassment.

Tremors are involuntary muscle contractions characterized by oscillations of a body part. Tremor of the hands can be cosmetically upsetting and affect functional tasks such as grasping of objects. Resting tremors usually occur at frequencies of approximately 4-7 Hz while the frequency of action of postural tremor is higher, usually between 9-11 Hz. Tremor is a symptom often targeted by treatment. The standard clinical method for analyzing rest and postural or action tremor is qualitative assessment by a clinician and assignment of a score.

Bradykinesia refers to delays or hesitations in initiating movements and slowness in executing movements. The standard clinical method for analyzing bradykinesia is qualitative assessment by a clinician and assignment of a score. This score is assigned while the subject completes a repetitive finger-tapping task, a repetitive hand opening-closing task, and a pronation-supination task. Objective assessment by this means is difficult and variable. It has been found that movement rate and time are useful in better characterizing bradykinesia.

Rigidity occurs because muscles of the body are overly excited. The neurons involved in inhibition circuitry have died due to Parkinson's disease and muscles may receive continuous excitation. Rigidity causes the joints of the subject to become stiff and decreases range of motion. During normal movement, an agonist muscle contracts while the antagonist muscles relax. However, due to the constant motor unit input, the antagonist is unable to relax. Again, the standard clinical method for analyzing rigidity is qualitative assessment by a clinician and assignment of a score. To do so a clinician passively moves the subject's joints through a range of motion while the subject relaxes.

Dyskinesia is one of the most common and disabling complications of chronic drug therapy. Dyskinesias are wild involuntary movements that typically occur when the benefit from the drug therapy is at its maximum. Clinical assessment of dyskinesias typically relies on self-reporting by the subject. There is a great need to objectively quantify these involuntary movements in view of the growing number of pharmacologic agents and surgical procedures to improve dyskinesia.

While standard clinical evaluation involves qualitative assessment of these symptoms, recently some efforts have been made to quantify symptoms of movement disorders. Accelerometers and gyroscopes have been used individually to quantify some of these movement disorder symptoms, however, alone each sensor has limitations. Accelerometers operate in response to the local gravitational field; therefore they often have problems in separating changes in linear acceleration from rotation. Further, results of a second integration required to obtain linear position are often contaminated with noise, making measurement difficult at best. Gyroscopes measure angular velocity independent of gravity with a good frequency response; however, static angular position cannot be measured accurately due to DC drift characteristic with these devices. Combining the information from both accelerometers and gyroscopes can provide a more accurate method of quantifying motion.

Currently, no commercially available system provides a means to objectively quantify the severity of movement disorder symptoms in real-time. Furthermore, many of these systems are bulky and cannot easily be worn by a subject during normal daily activities so as a result can only be used to monitor the subject in an intermittent fashion. In addition, some of these systems are tethered, which reduces patient safety, limits home monitoring capabilities, and does not allow for recording of some movement disorder symptoms. Finally, none of the current systems have clinician interface software, which quantifies symptoms such as tremor, bradykinesia, rigidity, and dyskinesias and relates them to standard rating scales such as the Unified Parkinson's Disease Rating Scale (UPDRS). Additionally, none of these systems have clinical video instruction and real-time clinical video feedback.

It is therefore an object of the present invention to provide a system for accurately quantifying symptoms of movement disorders. It is still another object of the present invention to provide a system, which accurately quantifies symptoms utilizing both kinetic information and electromyography (EMG) data. It is still another object of the present invention to provide a wireless movement disorder system that can be worn continuously to provide continuous information to be analyzed as needed by the clinician. It is still further another object of the present invention to provide a movement disorder system that can provide analysis in real-time. It is still further another object of the present invention to provide a movement disorder system to allow for home monitoring of symptoms in subject's with these movement disorders to capture the complex fluctuation patterns of the disease over the course of days, weeks or months. It is still further an object of the present invention to maximize subject safety. It is still further an object of the present invention to provide a system with clinical video instruction and real-time clinical video feedback. It is still further an object of the present invention to provide a treatment delivery system that can monitor symptoms in subject's and deliver treatment in response to those symptoms. Finally it is the object of the present invention to provide remote access to the clinician or physician.

SUMMARY OF THE INVENTION

The present invention relates to a movement disorder monitor, and a method of measuring the severity of a subject's movement disorder. The present invention additionally relates to a treatment delivery system including drugs for treating or dosing a subject in response to changes in the severity of a subject's symptoms.

The present invention provides for a system and method, which can accurately quantify symptoms of movements disorders, accurately quantifies symptoms utilizing both kinetic information and electromyography (EMG) data, that can be worn continuously to provide continuous information to be analyzed as needed by the clinician, that can provide analysis in real-time, that allows for home monitoring of symptoms in subject's with these movement disorders to capture the complex fluctuation patterns of the disease over the course of days, weeks or months, that maximizes subject safety, and that provides remote access to the clinician or physician.

In one embodiment, the present invention includes a portable movement disorder device for measuring severity of a subject's movement disorder comprising a first sensor for measuring a subject's external body motion having a signal related to the external body motion; and a second sensor for measuring a subject's electrical muscle activity wherein the severity of the subject's movement disorder is calculated based in part on the signals of the first and second sensors.

In another embodiment, the present invention includes a method of measuring severity of a subject's movement disorder comprising the steps of measuring a subject's external body motion; transmitting wirelessly a signal based in part on the subject's measured external body motion; receiving the wirelessly transmitted signal; and scoring the severity of a subject's movement disorder based in part on the wirelessly transmitted signal.

In still another embodiment, the present invention includes a portable movement disorder device or system for measuring severity of a subject's movement disorder comprising at least one sensor having a signal for measuring a subject's external body motion or physiological signal associated with a movement disorder; at least one processor for receiving the signal, and calculating the severity of the subject's movement disorder in real time.

In still another embodiment, the present invention includes a portable movement disorder device or system for measuring severity of a subject's movement disorder comprising at least one sensor having a signal for measuring a subject's external body motion or physiological signal associated with a movement disorder; recording that data to memory on the device, downloading that data to a computer at a later time and calculating the severity of the subject's movement disorder.

In still another embodiment, the present invention includes a drug delivery system comprising at least one sensor having a signal for measuring a subject's external body motion or physiological signal associated with a movement disorder; an actuator which allows a medication to be delivered from a reservoir external to the subject to a point internal to the subject; and a closed-loop control system for activating and deactivating the actuator based in part on the signal from the at least one sensor.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DESCRIPTION OF THE PREFERRED EMBODIMENT

Figure 1:
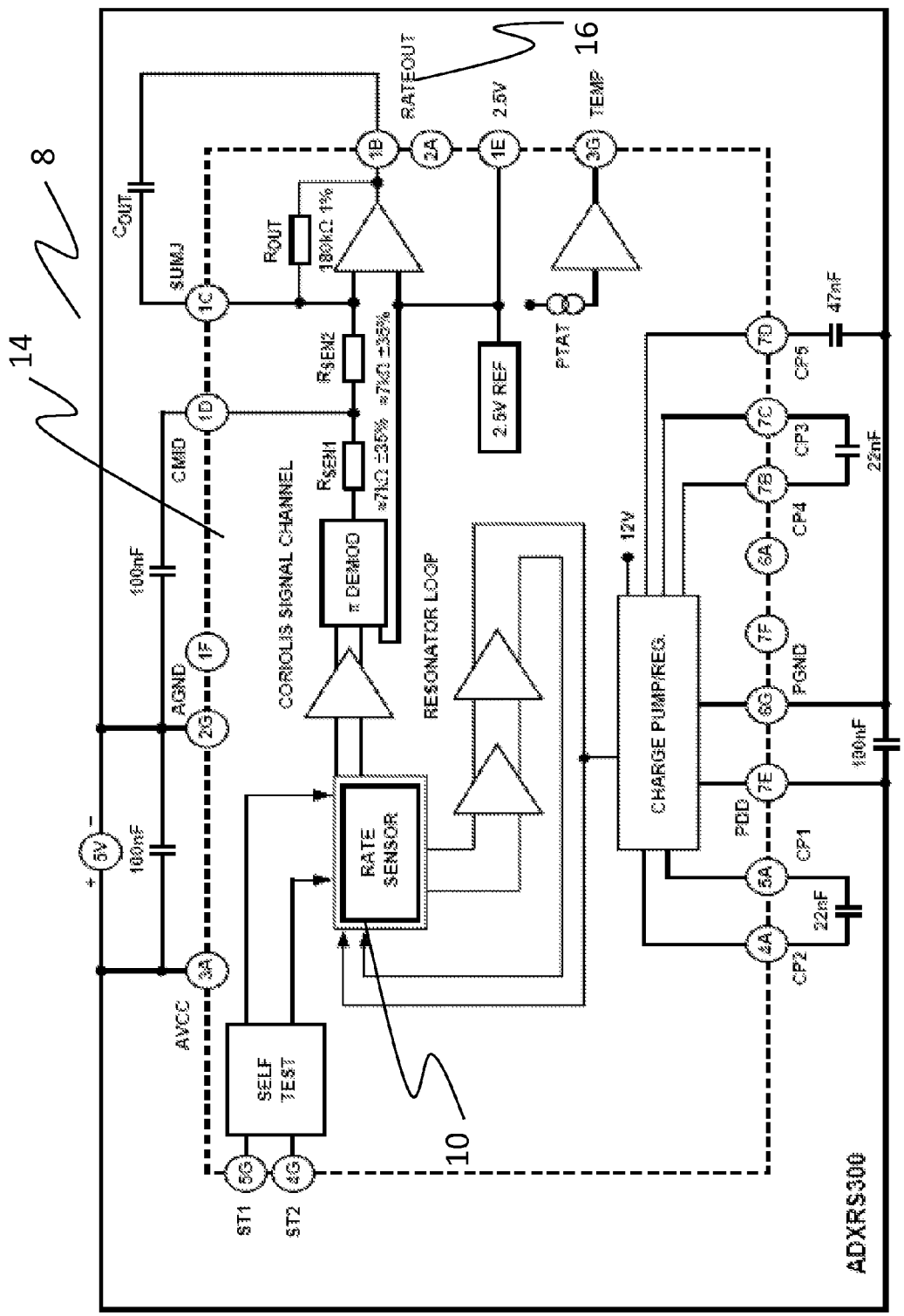
FIG. 1. Electrical schematic of a gyroscope useful in the present invention.

The present invention relates to a movement disorder monitor, and a method of measuring the severity of a subject's movement disorder. The present invention additionally relates to a drug delivery system for dosing a subject in response to the increased severity of a subject's symptoms.

The devices, systems and methods of the various embodiments of the present invention are used to analyze, score, and treat various movement disorders. Movement disorders for purposes of this application include but are not limited to Parkinson's disease (PD) and essential tremor. Some of the treatments used for these disorders involve pharmaceutical interventions, fetal cell transplants, surgery, or deep brain stimulation. The efficacy of these interventions is often judged by the interventions ability to alleviate patient symptoms and improve their quality of life. The subject on which the devices, system or method is used is a human or other form of animal.

The devices of the various embodiments of the present invention are preferably portable. By portable it is meant among other things that the device is capable of being transported relatively easily. Relative easy in transport means that the device can be carried by a single person, generally in a carrying case to the point of use or application. Furthermore the device preferably should be relatively light-weight. By relatively light-weight, preferably the device weighs less than about 3 lbs., more preferably less than about 2 lbs., even more preferably less than about 1 lb., and most preferably less than about 0.5 lbs. By being light-weight and further compact, the device should gain greater acceptance for use by the subject. The system for measuring and calculating the severity of the symptoms including external computers preferably weighs less than about 15 lbs., more preferably less than about 10 lbs., and most preferably less than about 5 lbs. This system more preferably can fit in a reasonably sized carrying case so the patient or their caregiver can easily transport the system.

Another advantage of the systems and methods of the present invention is the ability to determine or calculate the severity of a subject's symptoms in real time. By real time it is meant that within 30 minutes the severity of a subject's symptoms can be calculated or determined. Preferably, the subject's symptoms can be calculated or determined in less than about 30 seconds, more preferably in less than about 1 second, even more preferably in less than about 0.1 seconds, and most preferably in less than about 0.01 seconds.

The devices of the various embodiments of the present invention can form part of a system for use by a physician, veterinarian, technician or clinician for analysis or evaluation of a subject's movement disorder; for pharmaceutical research; or for delivery of pharmaceutical compounds. Other elements of this system may include but are not limited to receivers, routers, communication devices, processors, displays, drug delivery devices and the like, some of which are described further in various embodiments described in more detail below.

Various embodiments of the present invention may include a sensor for measuring a subject's external body motion. Many types of sensors are known by those skilled in the art for measuring external body motion. These sensors include but are not limited to accelerometers, gyroscopes, magnetometers, resistive bend sensors, combinations thereof, and the like. Preferably, a combination using an accelerometer and gyroscope is used. FIG. 1 is an electrical schematic diagram for one embodiment of a gyroscope 8 used as a sensor or in a sensor of the present invention. The sensor element 10 functions on the principle of the Coriolis Effect and a capacitive-based sensing system. Rotation of the sensor 10 causes a shift in response of an oscillating silicon structure resulting in a change in capacitance. An application specific integrated circuit (ASIC) 14, using a standard complimentary metal oxide semiconductor (CMOS) manufacturing process, detects and transforms changes in capacitance into an analog output voltage 16, which is proportional to angular rate. The sensor element design utilizes differential capacitors and symmetry to significantly reduce errors from acceleration and off-axis rotations.

Figure 2:
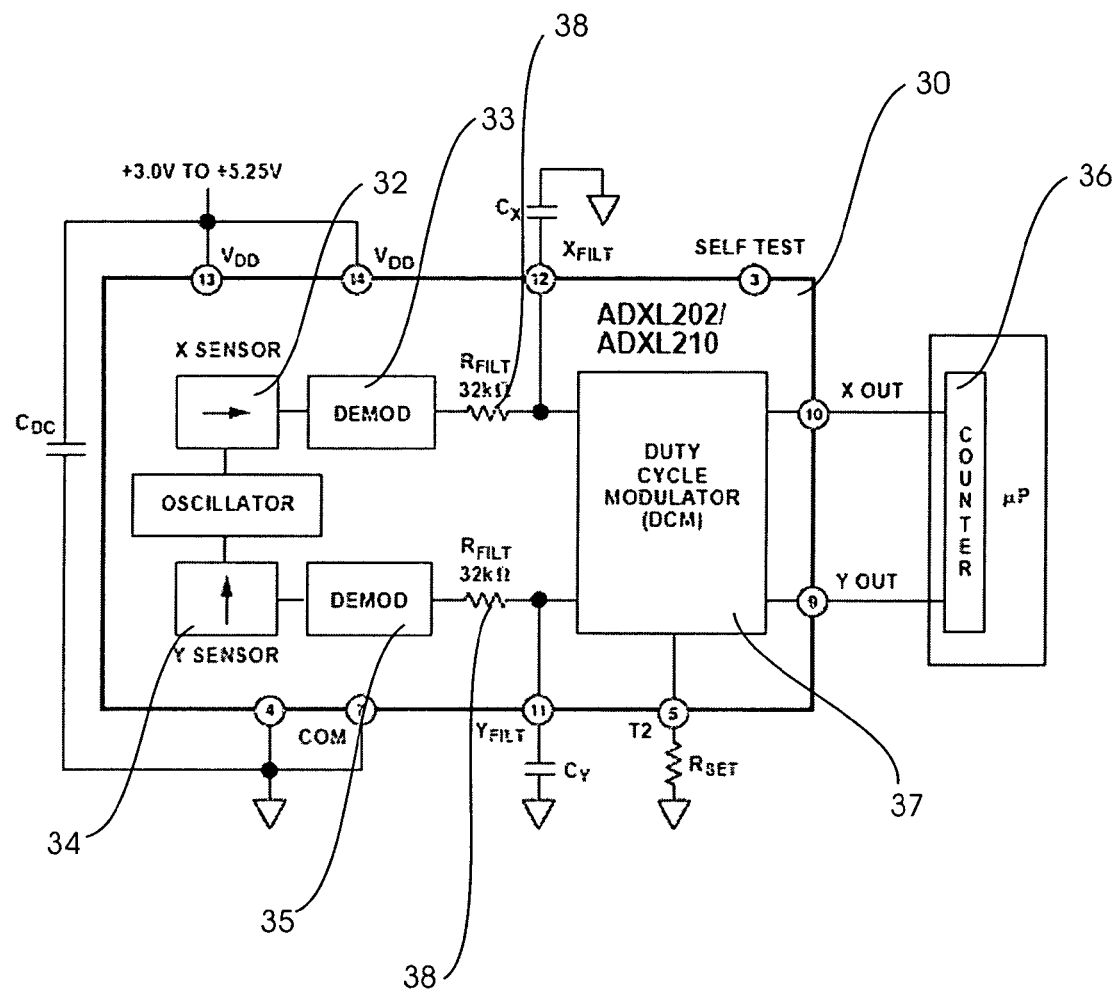
FIG. 2. Electrical schematic of a dual axis accelerometer useful in the present invention.

FIG. 2 is an electrical schematic diagram for one embodiment of a dual axis accelerometer of the present invention. The dual axis acceleration measurement system 30 is on a single monolithic IC. They contain a polysilicon surface-micromachined sensor and signal conditioning circuitry to implement an open-loop acceleration measurement architecture. For each axis 32, 34 an output circuit converts the analog signal to a duty cycle modulated (DCM) digital signal that can be decoded with a counter/timer port 36 on a microprocessor. The dual axis accelerometer is capable of measuring both positive and negative accelerations. The sensor 30 is a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree ∟ out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator 33, 35 drives a duty cycle modulator (DCM) 37 stage through a 32 kOhm ☐ resistor 38. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage 37. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

Figure 3:
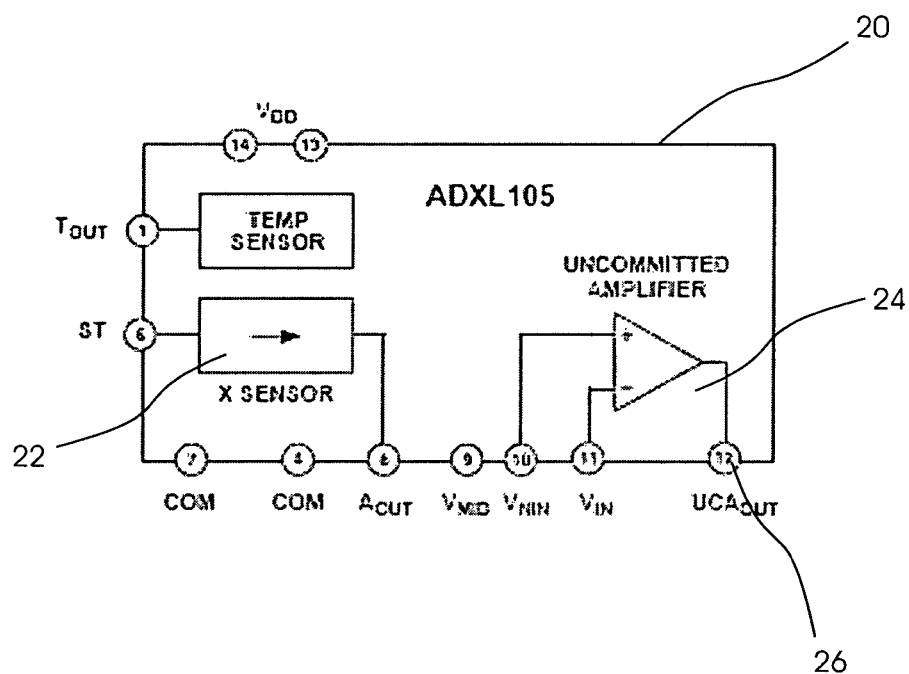
FIG. 3. Electrical schematic of a single axis accelerometer useful in the present invention.

FIG. 3 is an electrical schematic diagram for one embodiment of a single axis accelerometer of the present invention. The accelerometer 20 is fabricated using a surface micromachining process. The fabrication technique uses standard integrated circuit manufacturing methods enabling all signal processing circuitry to be combined on the same chip with the sensor 22. The surface micro-machined sensor element 22 is made by depositing polysilicon on a sacrificial oxide layer that is then etched away leaving a suspended sensor element. A differential capacitor sensor is composed of fixed plates and moving plates attached to the beam that moves in response to acceleration. Movement of the beam changes the differential capacitance, which is measured by the on chip circuitry. All the circuitry 24 needed to drive the sensor and convert the capacitance change to voltage is incorporated on the chip requiring no external components except for standard power supply decoupling. Both sensitivity and the zero-g value are ratiometric to the supply voltage, so that ratiometeric devices following the accelerometer (such as an analog to digital converter (ADC), etc.) will track the accelerometer if the supply voltage changes. The output voltage (VOUT) 26 is a function of both the acceleration input and the power supply voltage (VS).

Figure 4A:
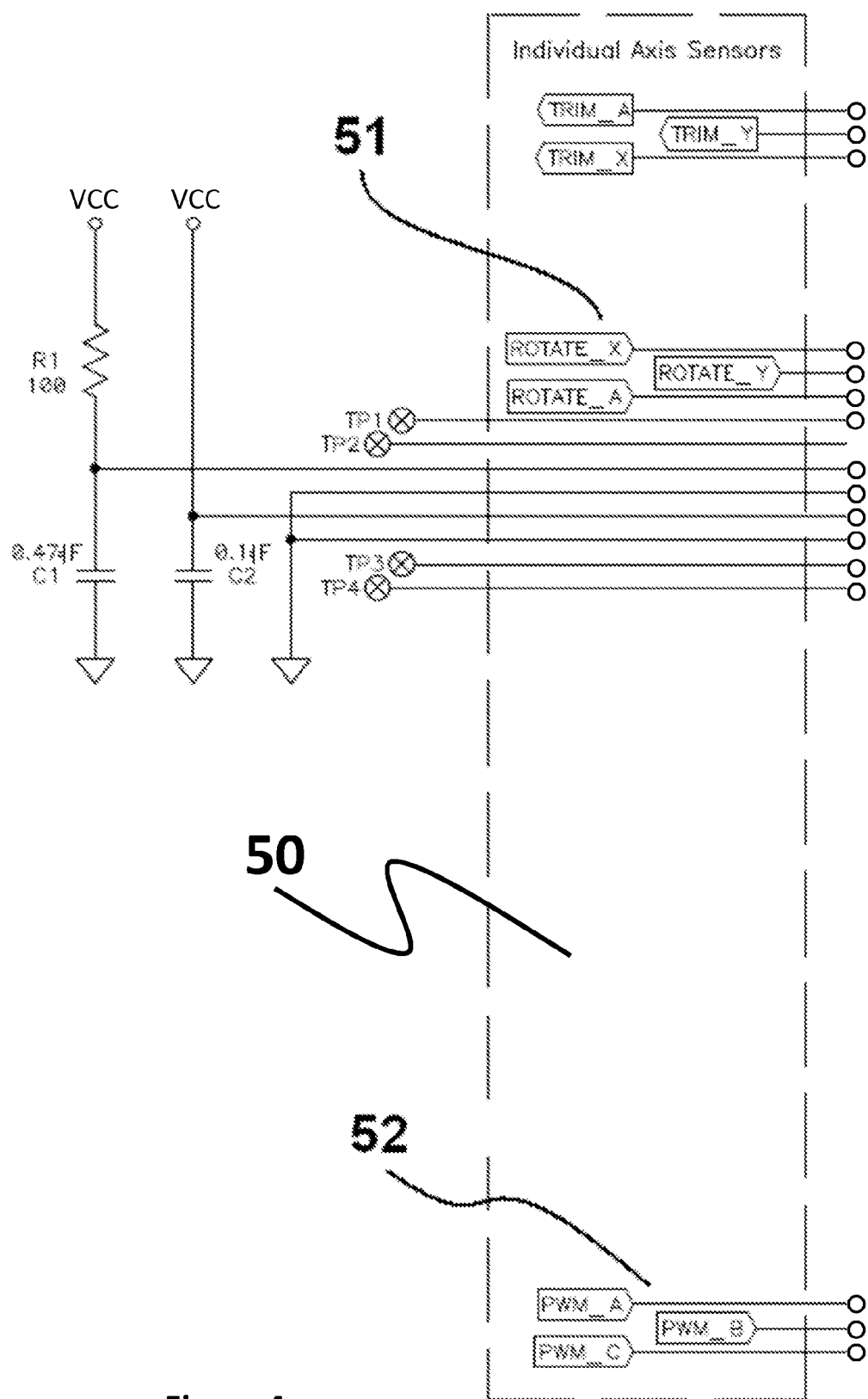
FIG. 4a-4c. Electronic Schematic of the Patient Worn sensor board unit.
Figure 4B:
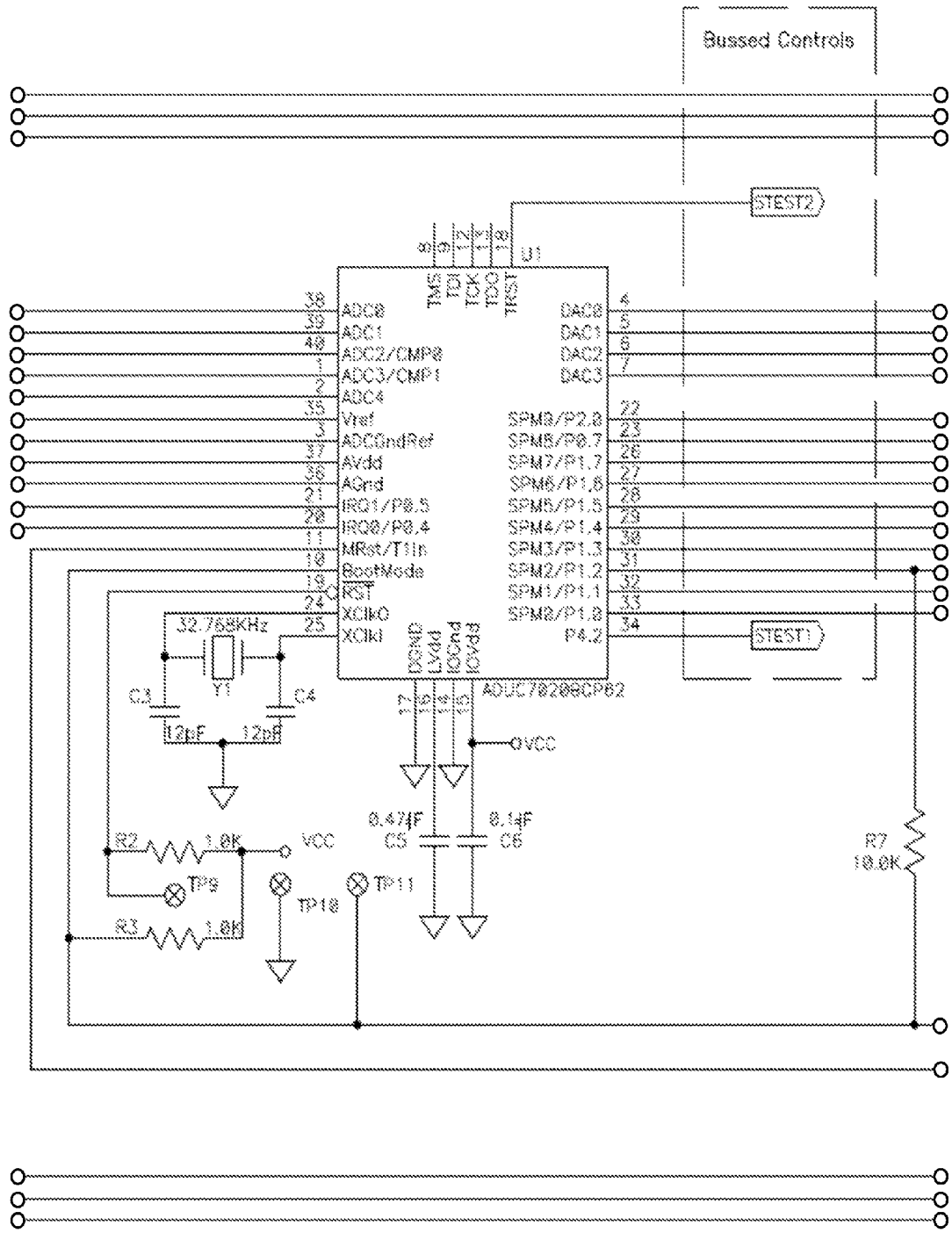
Figure 4C:
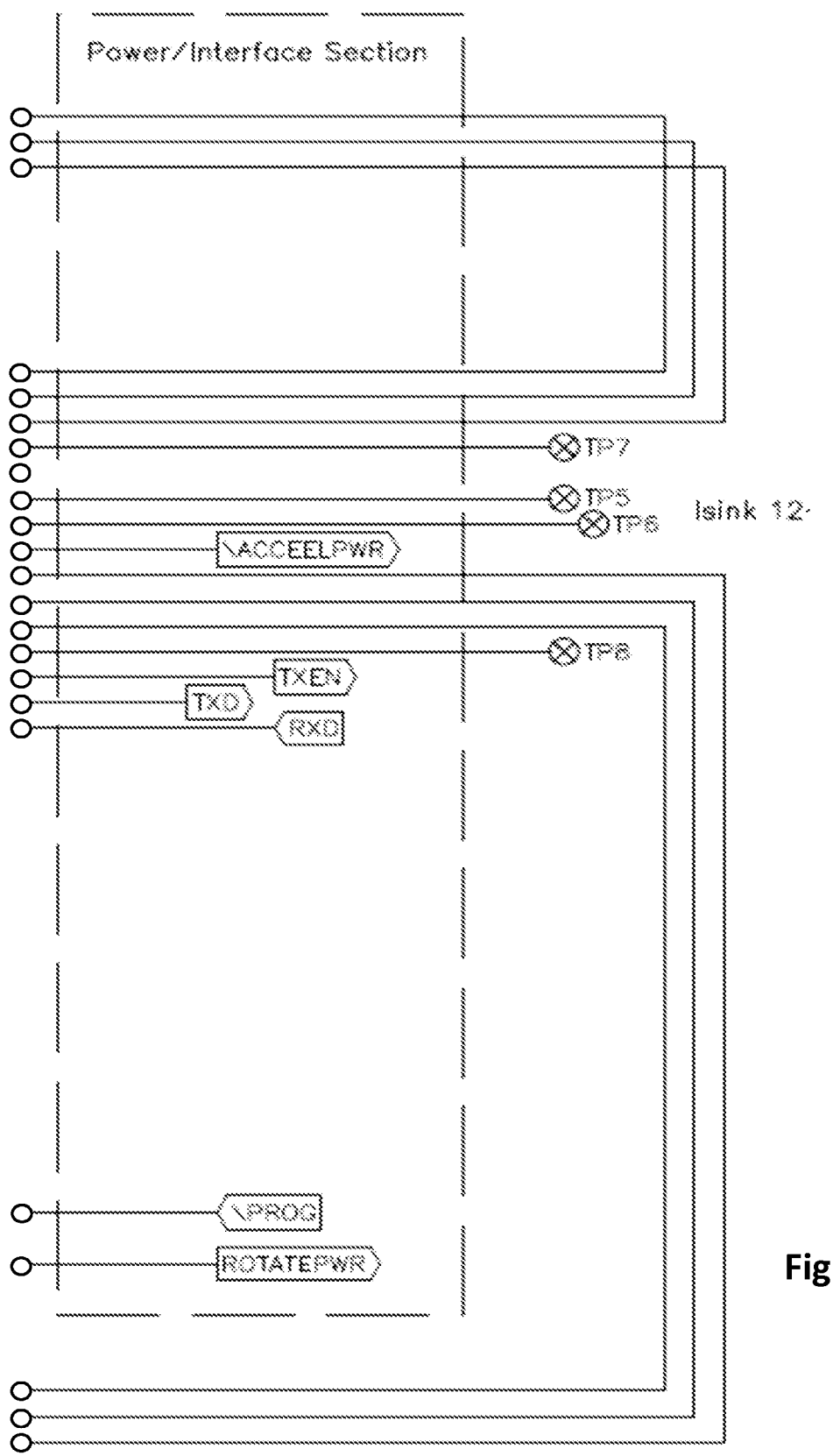
Figure 5A:
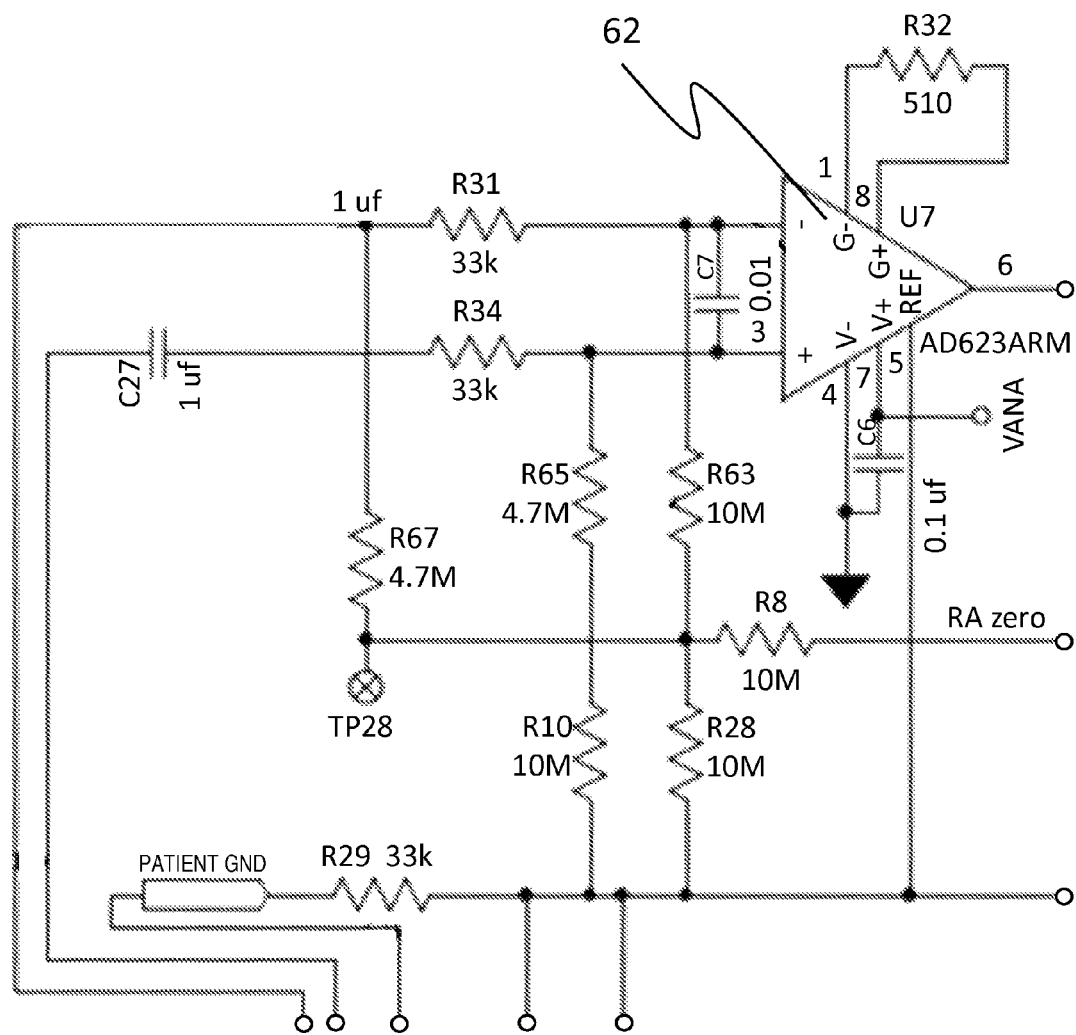
FIGS. 5a-5i. Exploded views of various sections of the Electronic Schematic of the Patient Worn transceiver module unit.
Figure 5B:
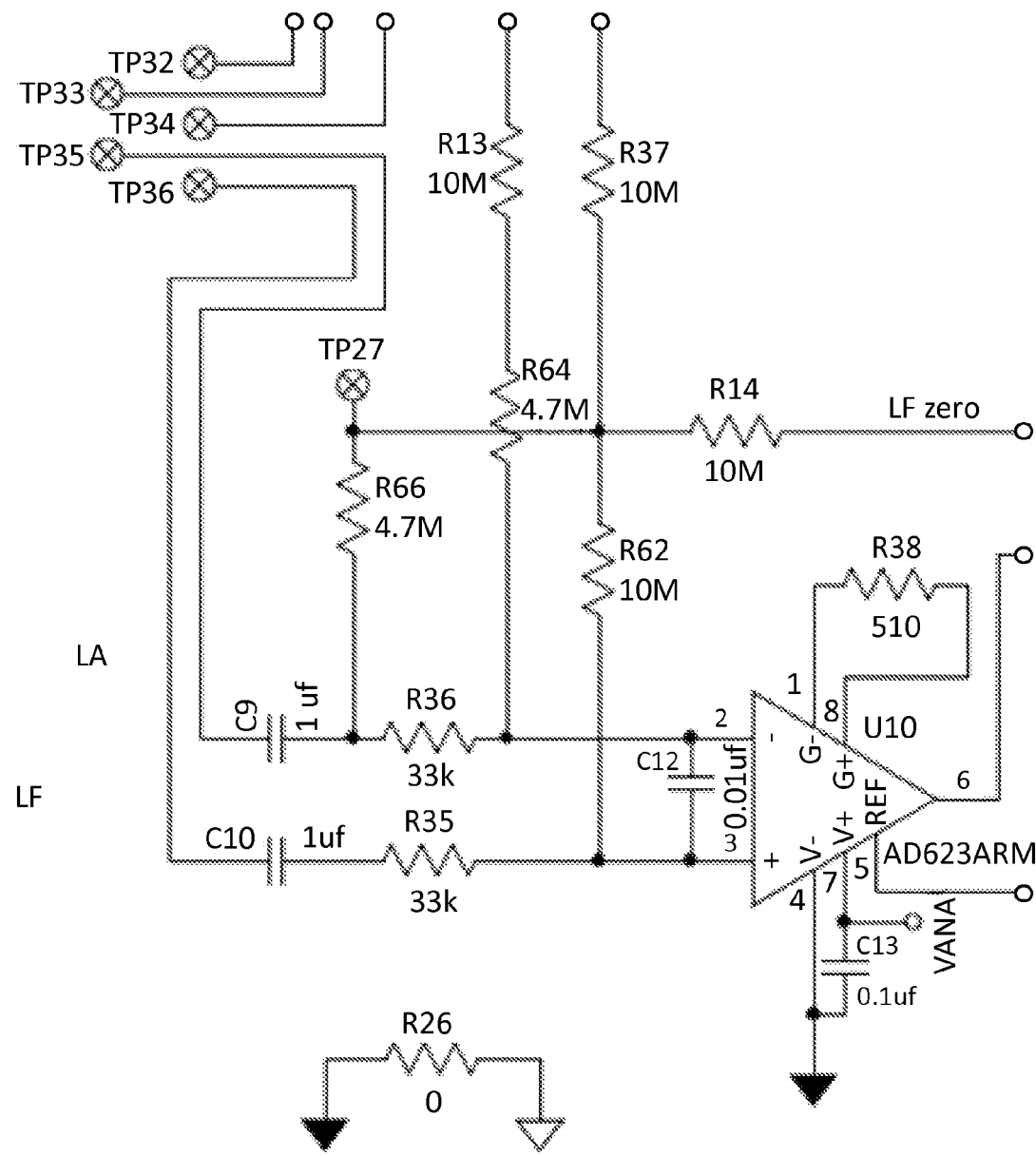
Figure 5C:
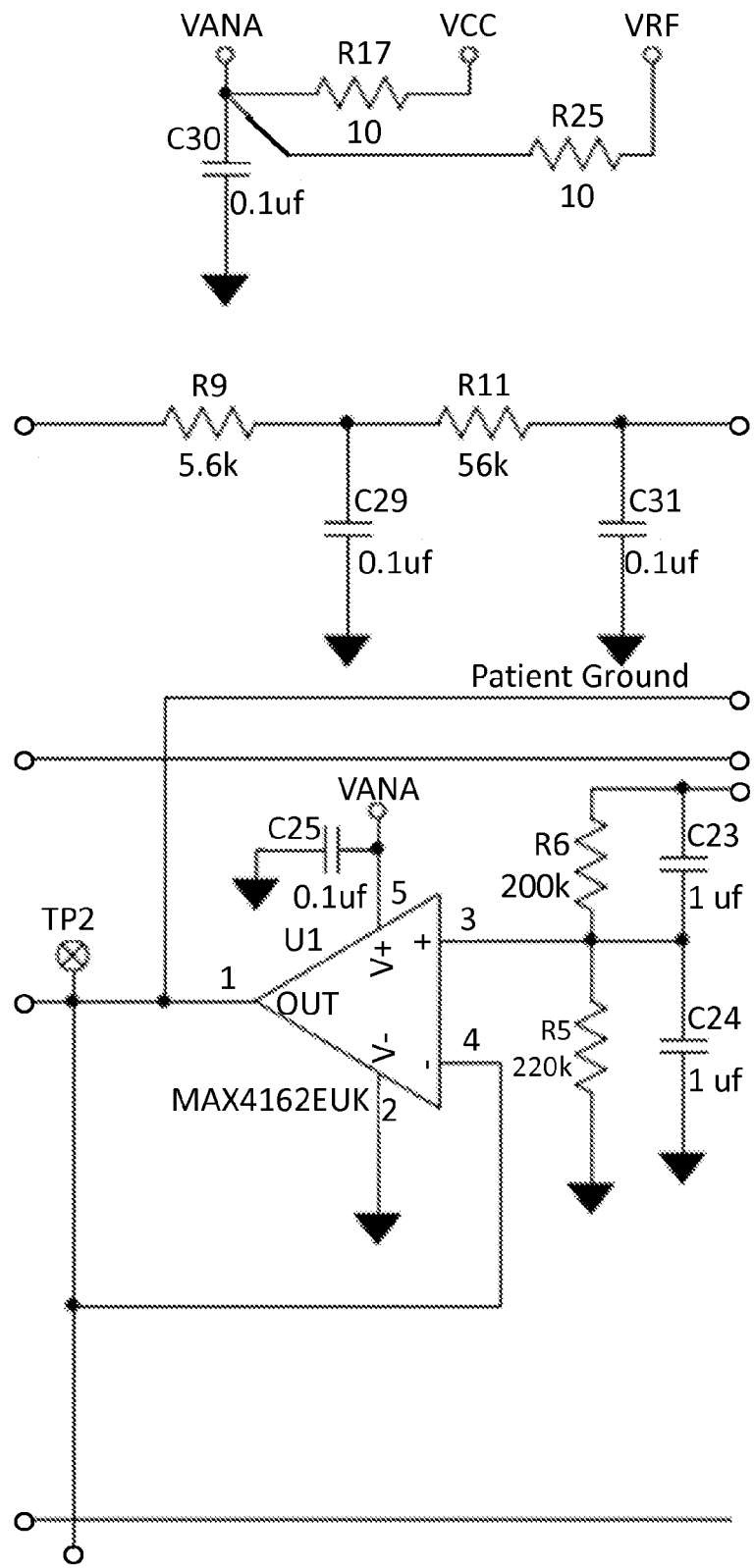
Figure 5D:
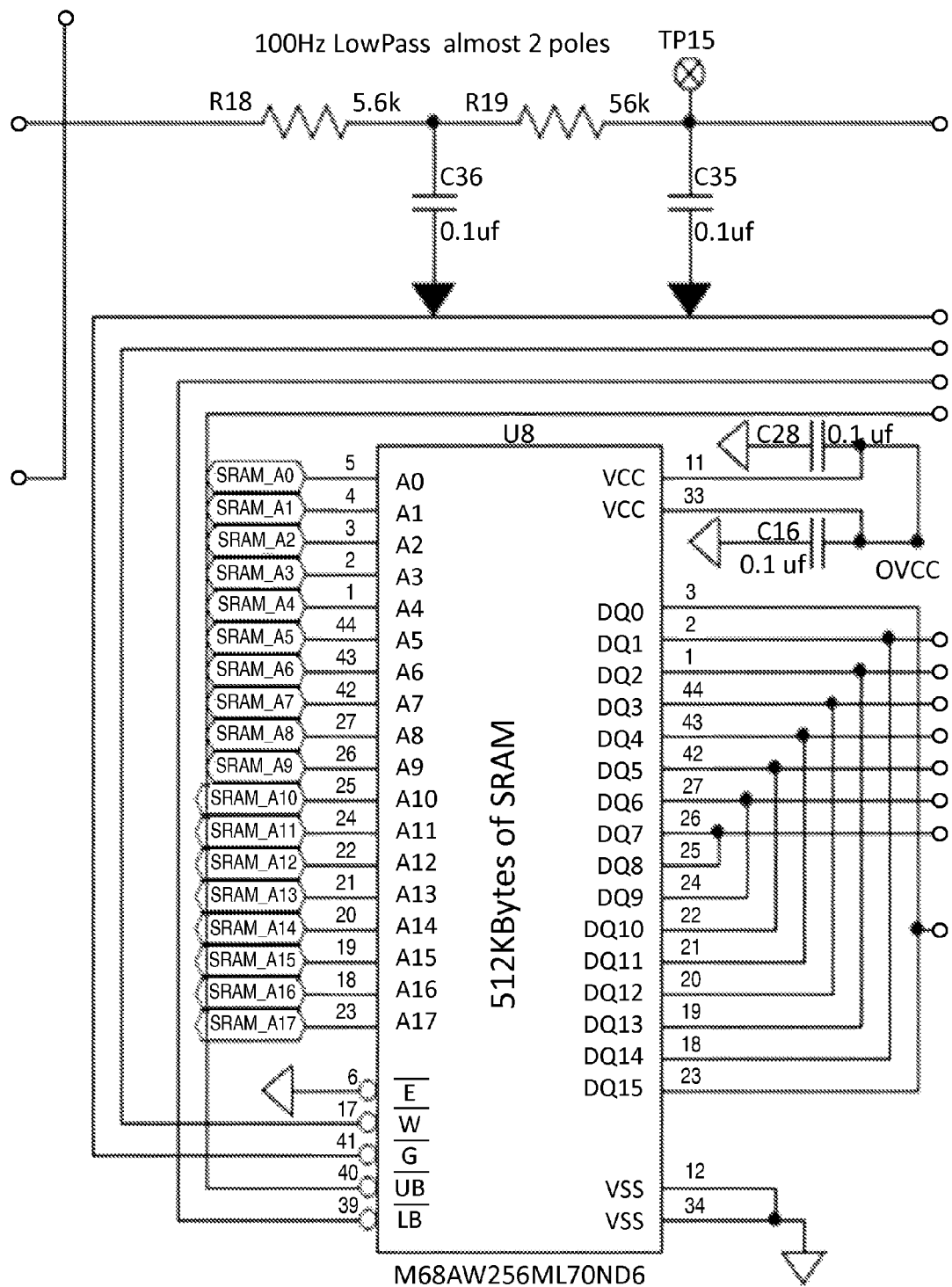
Figure 5E:
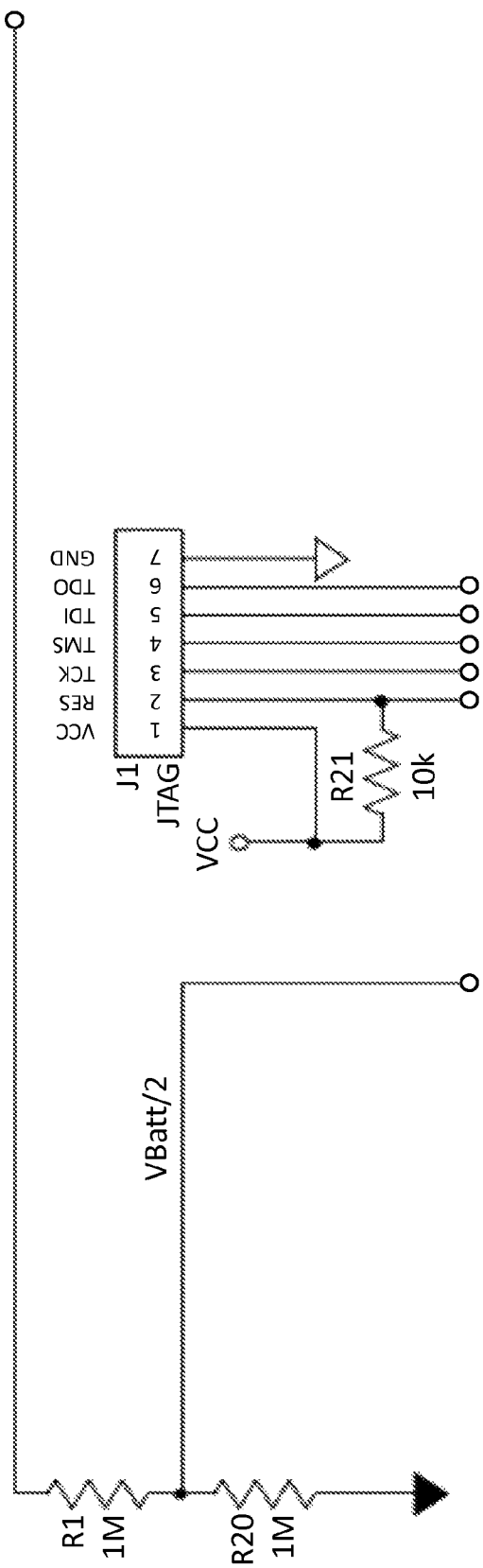
Figure 5F:
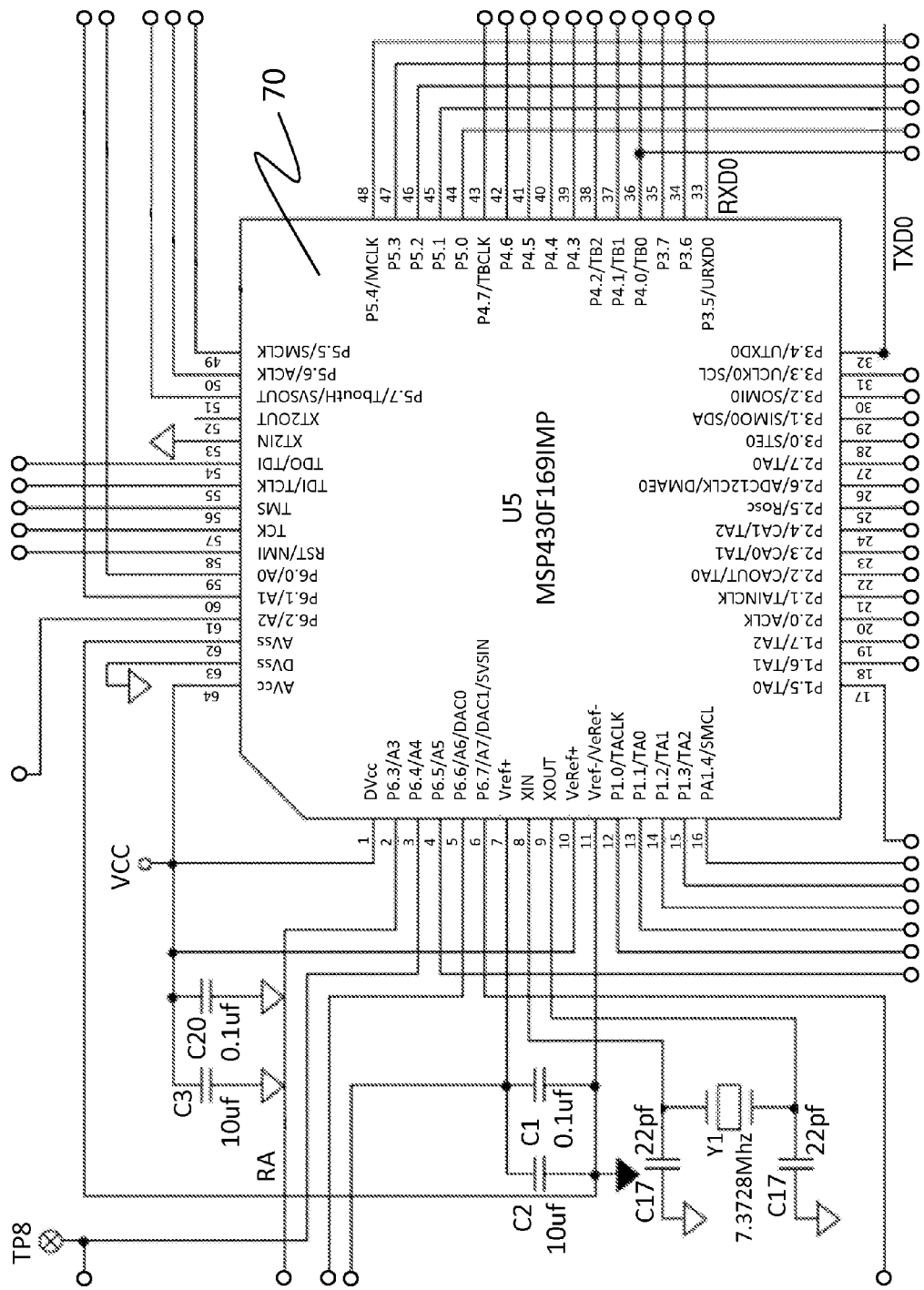
Figure 5G:
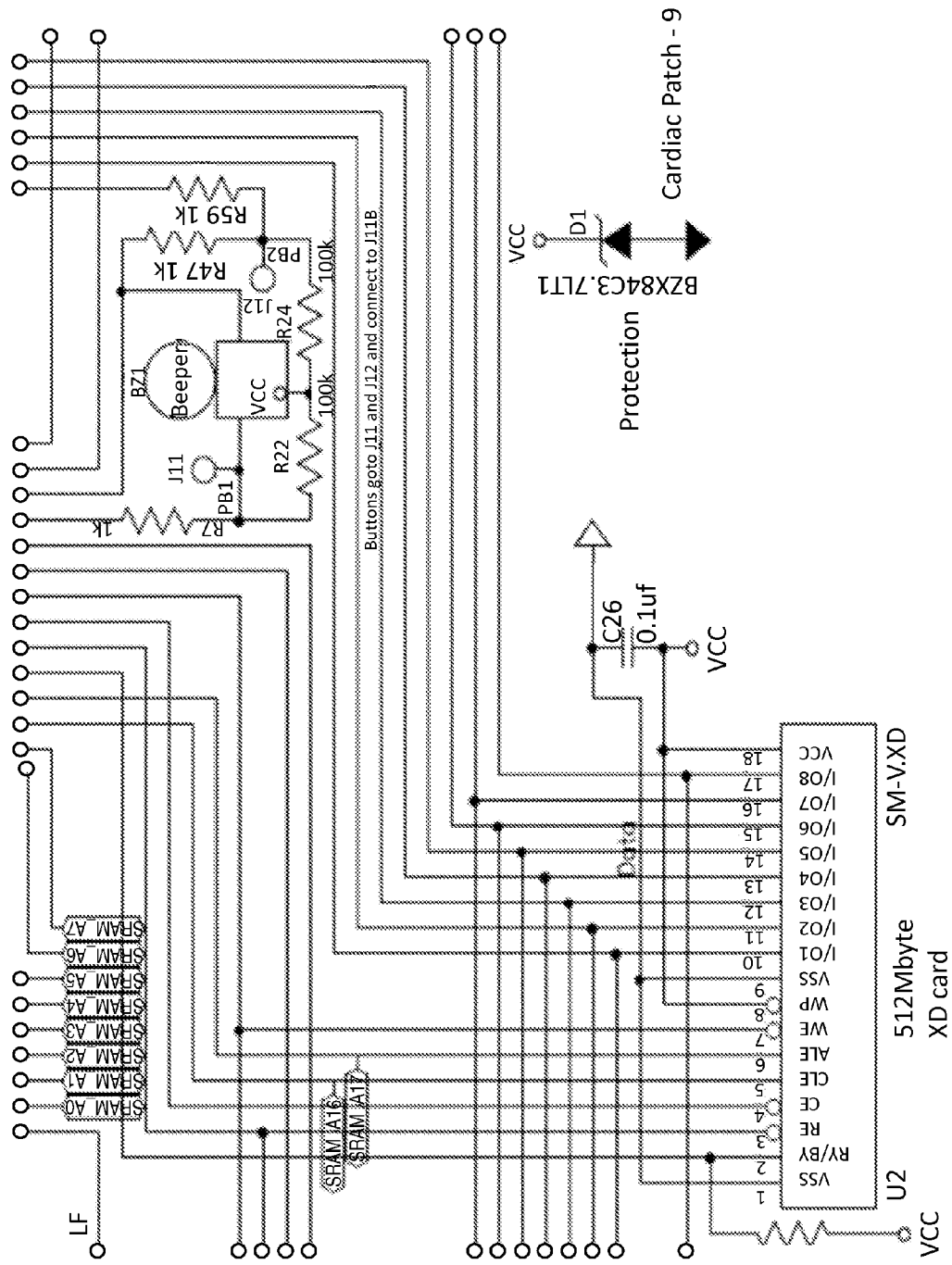
Figure 5H:
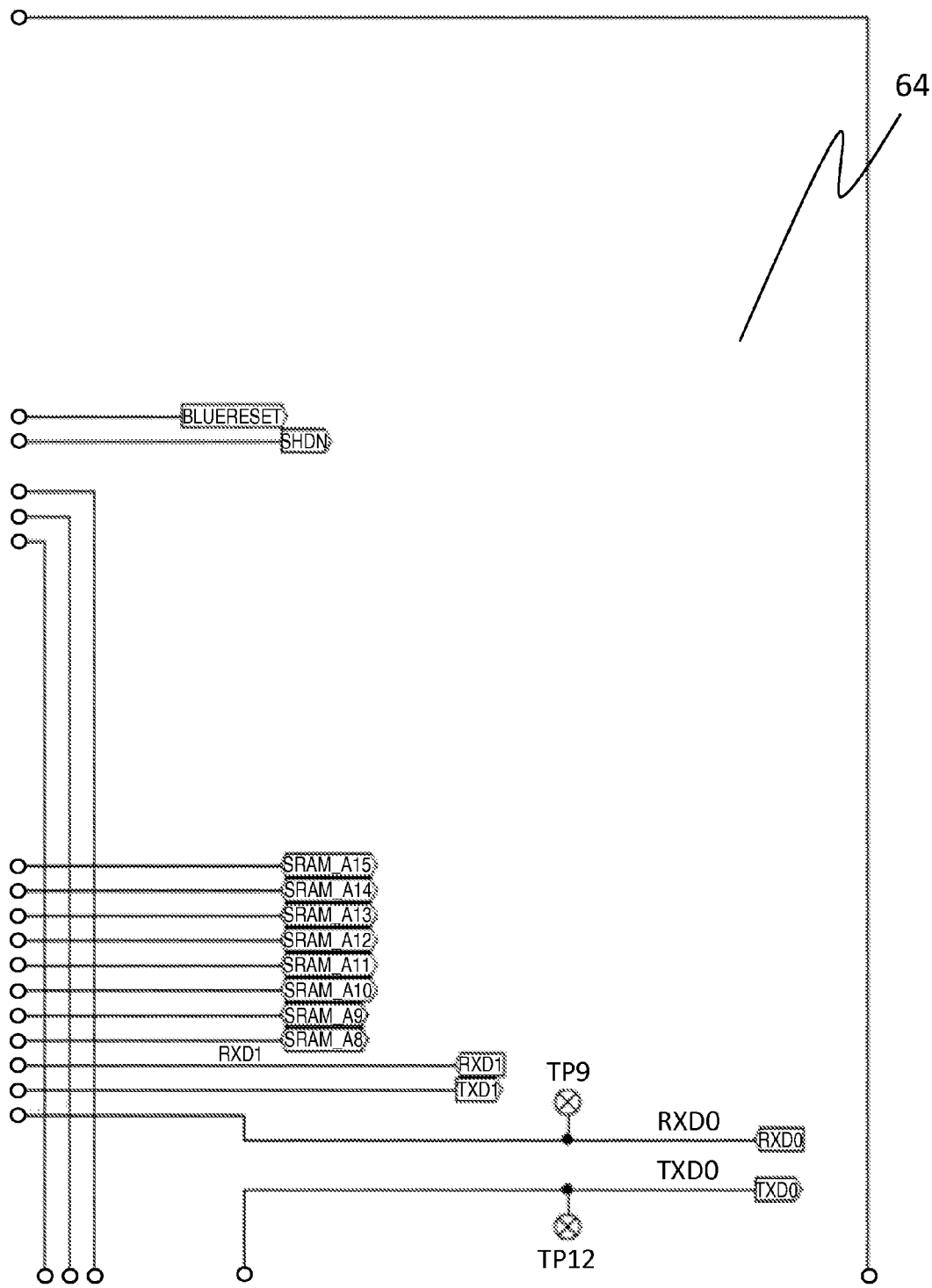
Figure 5I:
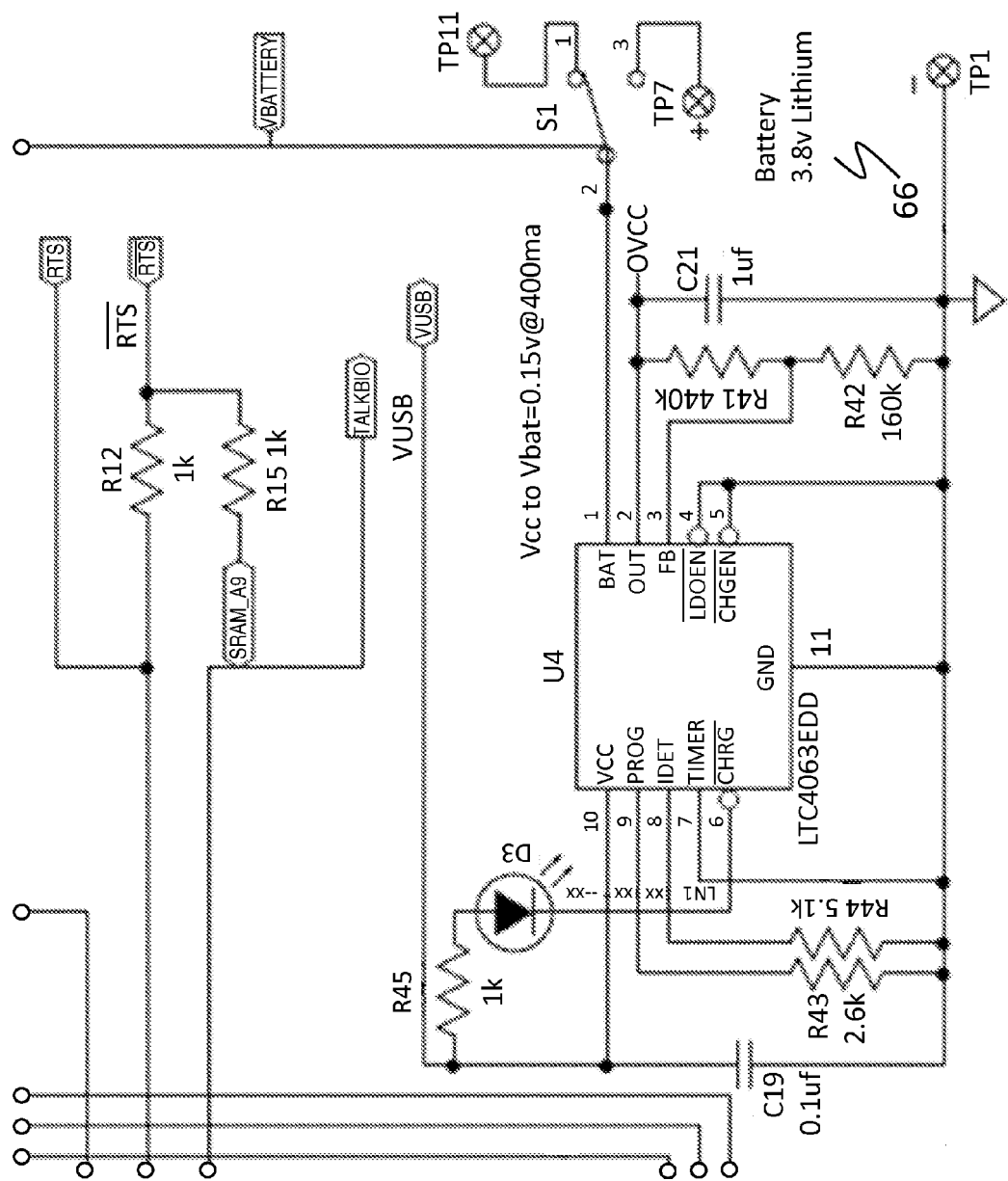

FIGS. 4a-4c illustrate an electrical schematic diagram for one embodiment of the subject worn sensor unit. FIG. 4a. shows a kinetic sensor board 50 (or subject worn external sensor) of the present invention. The kinetic sensor board 50 is preferably configured with both an accelerometer and a gyroscope for quantifying the subject's motion. In this particular embodiment, the kinetic sensor board 50 consists of three gyroscopes 51 and three orthogonal accelerometers 52. The kinetic sensor board also includes a microprocessor (Texas Instruments mSP430-169) and a power interface section.

FIG. 5 is an electrical schematic diagram for one embodiment of the subject worn transceiver module 64. Exploded views of various sections of the electrical schematic diagram are shown in FIGS. 5a-5i. The transceiver module includes a blue tooth radio (EB100 A7 Engineering) to provide wireless communications with the patient PC, EMG amplifier and data acquisition circuitry, on board memory, a microprocessor 70, FIGS. 5 and 5*f*, (Analog Devices ADVC7020), and a battery power supply (lithium powered) 66, FIG. 5*i* that supplies power to both the transceiver module 64, FIG. 5*h*, and one or more external sensor modules 50. The transceiver module also includes a USB port to provide battery recharging and serial communications with the patient PC. The transceiver module also includes a push button input. The transceiver module also includes a limo connector to attached EMG electrode leads to the module.

Figure 6:
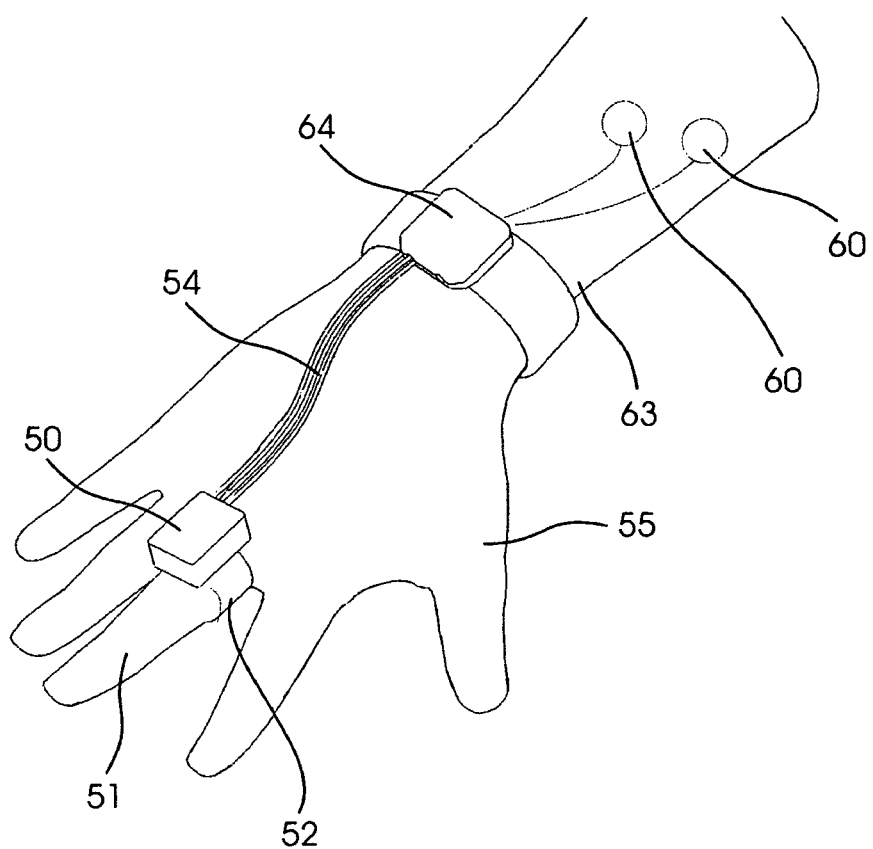
FIG. 6. Schematic showing placement of various components of the movement disorder device with an external sensor module for the hand and EMG electrodes.

FIG. 6 illustrates one possible embodiment of the subject 55 worn components of the system combining the sensor board 50 and the transceiver module 64. The sensor board 50 is worn on the subject's 55 finger 51 and the transceiver module 64 is worn on the subject's 55 wrist 63. The transceiver module 64 and one or more external sensor modules 50 are connected by a thin multi-wire leads 54. The transceiver module 64 in this embodiment connects to one or more electrodes 60 used to measure EMG.

Figure 7:
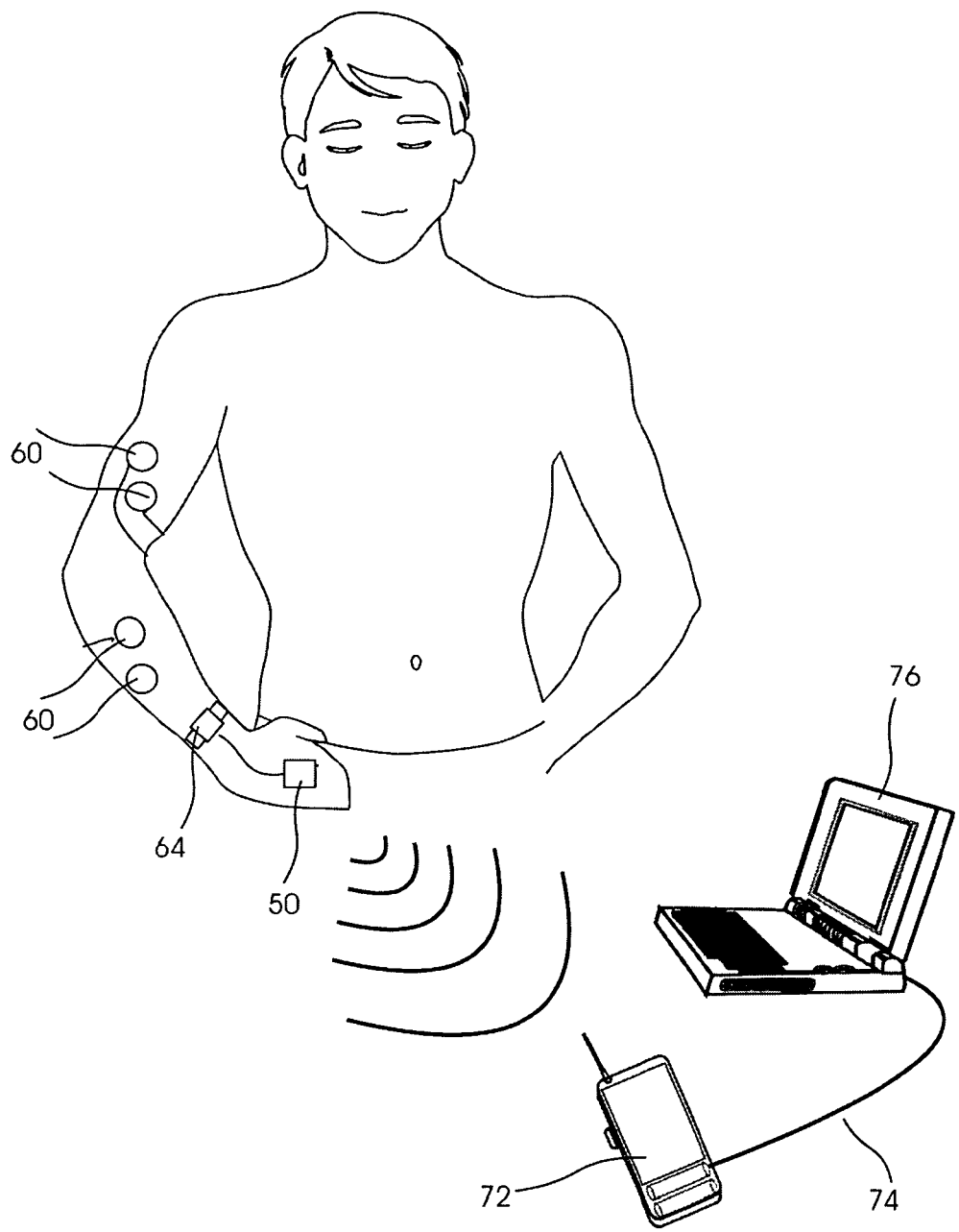
FIG. 7. Schematic showing various system components of the movement disorder device.

FIG. 7 illustrates one embodiment of the system components of the wireless movement disorder monitor. The external sensor module 50 in this embodiment contains three orthogonal accelerometers (not shown) and three orthogonal gyroscopes (not shown). This input to the external sensor module 50 consists of the kinetic forces applied by the user and measured by the accelerometers and gyroscopes. The output from the board is linear acceleration and angular velocity data in the form of output voltages. These output voltages are input to the transceiver module 64. These voltages undergo signal conditioning and filtering before sampling by an analog to digital converter. This digital data is then stored in on board memory and/or transmitted as a packet in RF transmission by a blue tooth transceiver. Additionally, EMG electrodes 60 worn by the subject may be input to the transceiver module. An amplifier on the transceiver module 64 amplifies the EMG signal(s) before signal conditioning, filtering, and sampling by the analog to digital converter. The EMG data is also stored in the on board memory and/or contained in the packet for RF transmission. A microprocessor (not shown) in the transceiver module 64 controls the entire process. Kinetic and EMG data packets may be sent by RF transmission to a nearby computer transceiver 72 which receives the data using an embedded blue tooth radio to a computer 76. Kinetic and EMG data may also be stored on the on board memory and downloaded to a computer 76 at a later time. The computer 76 then processes, analyzes, and stores the data. The kinetic sensor board 50 measures accelerations along and angular velocities about each of three orthogonal axes. The signals from the accelerometers and gyroscopes of the kinetic sensor board 50 are preferably input into a processor for signal conditioning and filtering. Preferably, three Analog Devices gyroscopes (ADXRS300) were utilized on the kinetic sensor board with an input range up to 1200 degrees/second. The Analog Devices parts were selected after an analysis of cost, size and power consumption. The ball grid array type of component was selected to minimize size. Additionally, a MEMS technology dual axis accelerometer, from Analog Devices (ADXL210), was employed to record accelerations along the x and y-axes. The sensors provide 80 dB dynamic range, low noise (1 mg/sqrt (Hz)), and low power (<2 mA per axis) in a surface mount package. Other combinations of accelerometers and gyroscopes known to those skilled in the art could also be used. A lightweight plastic housing was then used to house the sensor for measuring the subject's external body motion. The external body motion sensor(s) can be worn on the subject's finger, hand, wrist, fore arm, upper arm, head, chest, back, legs, feet and/or toes.

Various embodiments of the present invention may include a sensor(s) for measuring the subject's electrical muscle activity through techniques such as electromyography (EMG) or the like. FIG. 7 shows the EMG electrodes 60 which are connected to an amplifier 62. With an EMG sensor, a voltage difference or difference in electrical potential is measured between at least two recording electrodes. The electrodes used can be any type known to those skilled in the art including both indwelling (needle), surface and dry electrodes. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out and no skin to abrade or clean. Additionally if electrodes are used as the sensor(s), preferably at least three electrodes are used—two signal electrodes and one reference electrode.

Preferably, the transceiver module 64 contains one or more electronic components such as the microprocessor 70 for detecting both the signals from the gyroscopes 51 and accelerometers 52, and for detecting the signal from EMG electrode 60. Preferably, the one or more electronic components also filter (and possibly amplify) the detected EMG signals and kinetic motion signals, and more preferably convert these signals, which are in an analog form into a digital signal for transmission to the remote receiving unit. The one or more electronic components are attached to the subject as part of device or system. Further preferably, the one or more electronic components can receive a signal from the remote receiving unit or other remote transmitters. The one or more electronic components may include circuitry for but are not limited to for example electrode amplifiers, signal filters, analog to digital converter, blue tooth radio, a DC power source and combinations thereof. The one or more electronic components may comprise one processing chip, multiple chips, single function components or combinations thereof, which can perform all of the necessary functions of detecting a kinetic or physiological signal from the electrode, storing that data to memory, uploading data to a computer through a serial link, transmitting a signal corresponding to a kinetic or physiological signal to a receiving unit and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.5 in$^2$, and most preferably less than 0.25 in$^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

Preferably, the circuitry of the one or more electronic components comprises data acquisition circuitry further including an amplifier that amplifies the EMG, (The gyroscope and accelerometer signals will not need to be amplified). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is the Texas Instruments MSP430-169 microcontroller. The Texas Instruments MSP430-169 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of the transceiver module comprises a digital section. More preferably, the heart of the digital section of the sensor board is the Analog Devices ADVC7020 microcontroller. The Analog Devices ADVC7020 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the system can be tested and calibrated without leaving any unnecessary electronic components or too large an PCB imprint area on the final unit.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a blue tooth radio system utilizing the EB100 component from A7 engineering. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the remote communication station. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes—a patient code, the remote communication station is capable of receiving and transmitting data to several subjects, and for evaluating the data if the remote communication station is capable of doing so. This is realized in a way such that the identification unit has control logic, as well as a memory for storing the identification codes. The identification unit is preferably programmed by radio transmission of the control characters and of the respective identification code from the programming unit of the remote communication station to the patient worn unit. More preferably, the unit comprises switches as programming lockouts, particularly for preventing unintentional reprogramming.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control sub architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The remote communication station of various embodiments of the present invention can be any device known to receive RF transmissions used by those skilled in the art to receive transmissions of data. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back. Further optionally, two different remote communication stations can be used, one for receiving transmitted data and another for sending data. For example, with the wireless movement disorder monitoring system of the present invention, the remote communication system of the present invention can be a wireless router, which establishes a broadband Internet connection and transmits the physiological signal to a remote Internet site for analysis, preferably by the subject's physician. Another example is where the remote communication system is a PDA, computer or cell phone, which receives the physiological data transmission, optionally re-processes the information, and re-transmits the information via cell towers, land phone lines or cable to a remote site for analysis. Another example is where the remote communication system is a computer or processor, which receives the data transmission and displays the data or records it on some recording medium, which can be displayed or transferred for analysis at a later time.

The digitized kinetic or physiological signal is then transmitted wirelessly to a remote communication station (FIG. 7). This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal based in part from the physiological signal from the remote communication station wirelessly or via the internet to another monitor, computer or processor system. This allows the physician or monitoring service to review the subjects physiological signals and if necessary to make a determination, which could include modifying the patients treatment protocols.

Optionally, the system of the present invention includes some form of instruction, which can be in written form on paper or on a computer monitor, or on a video. Preferably, a video is used which instructs the subjects to perform a series of tasks during which their kinetic motion and/or EMG can be measured. Since the system of the present invention is preferably used in the subject's home, a video giving directions and/or describing various tasks to be performed by the subject is included with the system. The video may be accessed or viewed for example but not by way of limitation through use of video tape, DVD, as part of computer software provided, through the internet, or the like. The directions could include but are not limited to instructions on how to don the device, how to turn the device on, and the like. The description of various tasks could include but is not limited to exercises which are typically used by a technician, clinician or physician to evaluate a subject with a movement disorder including but not limited to hand grasps, finger tapping exercises, other movements and the like. One embodiment of a video includes the technician, clinician or physician looking into the camera, as they would a patient, and instructing them on device setup, instructing the patients through each of the tasks to be performed, providing verbal encouragement via video after a task, and asking subject's to repeat a task if it was not completed. Preferably, these video clips are edited and converted to a MPEG files using a Pinnacle Studios digital video system that includes a fire-wire card and editing software. For movement disorders such as Parkinson's disease preferably the technician, clinician or physician instructs the user through multiple tasks as per the UPDRS guidelines including but not limited to rest tremor, postural tremor, action tremor, all bradykinesia tasks (including but not limited to finger taps, hand grasps, and pronation/supination tasks), and/or rigidity tasks. More preferably, if the video is linked to the user interface software, the software will automatically detect if a subject has performed the requested task and provide feedback through the video to either repeat the task or continue to the next task.

The present invention includes various methods of measuring and scoring the severity of a subject's movement disorder. These methods include a number of steps which may include but are not limited to measuring a subject's external body motion; transmitting wirelessly a signal based in part on the subject's measured external body motion; receiving the wirelessly transmitted signal; downloading data from memory; and scoring the severity of a subject's movement disorder based in part on the wirelessly transmitted or downloaded signal. Optionally, an electromyogram of the subject's muscle activity may be obtained and used in part to score the severity of the subject's movement disorder.

Figure 8:
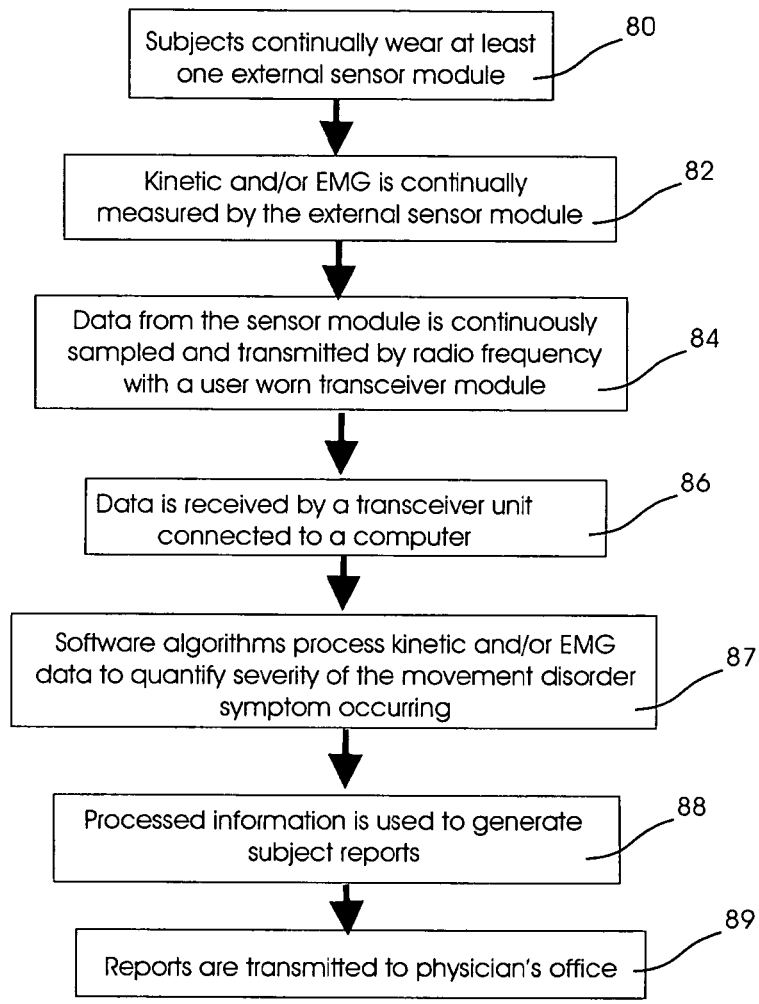
FIG. 8. Flow diagram of system in continuous operating mode.
Figure 9:
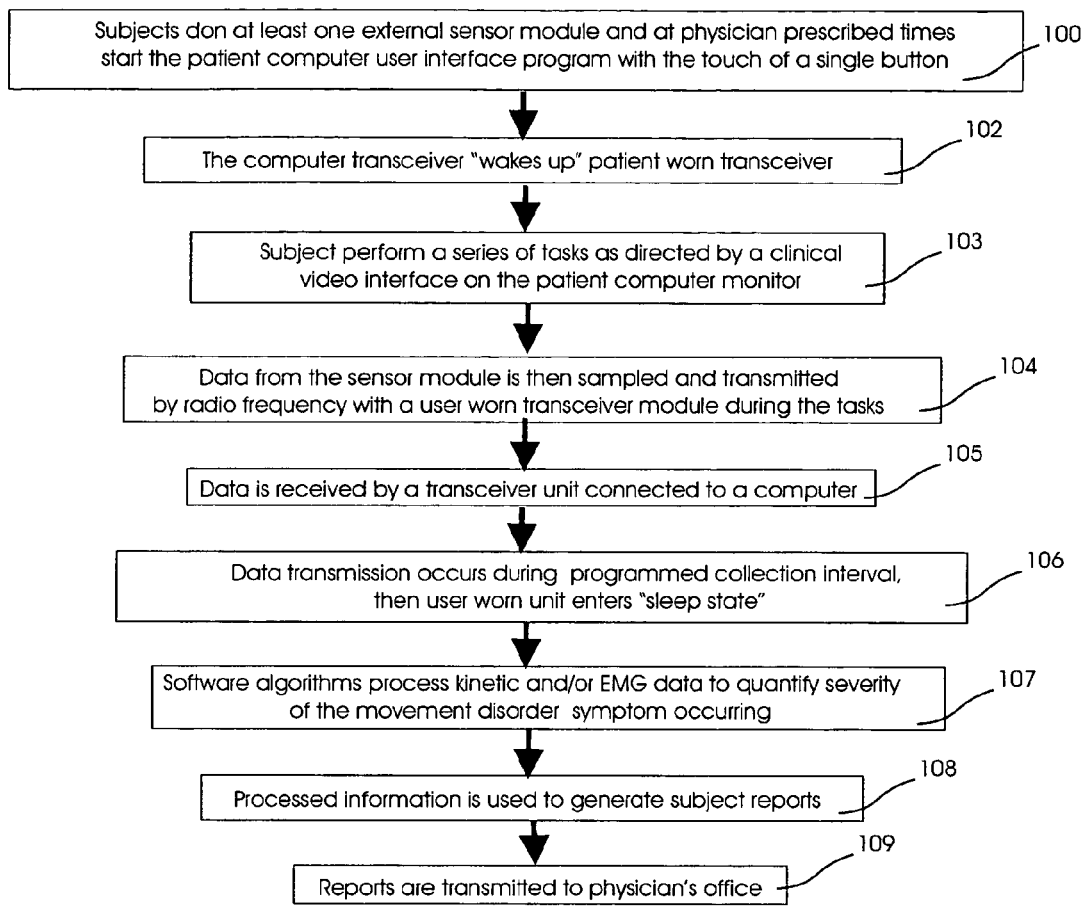
FIG. 9. Flow diagram of system in task operating mode.
Figure 10:
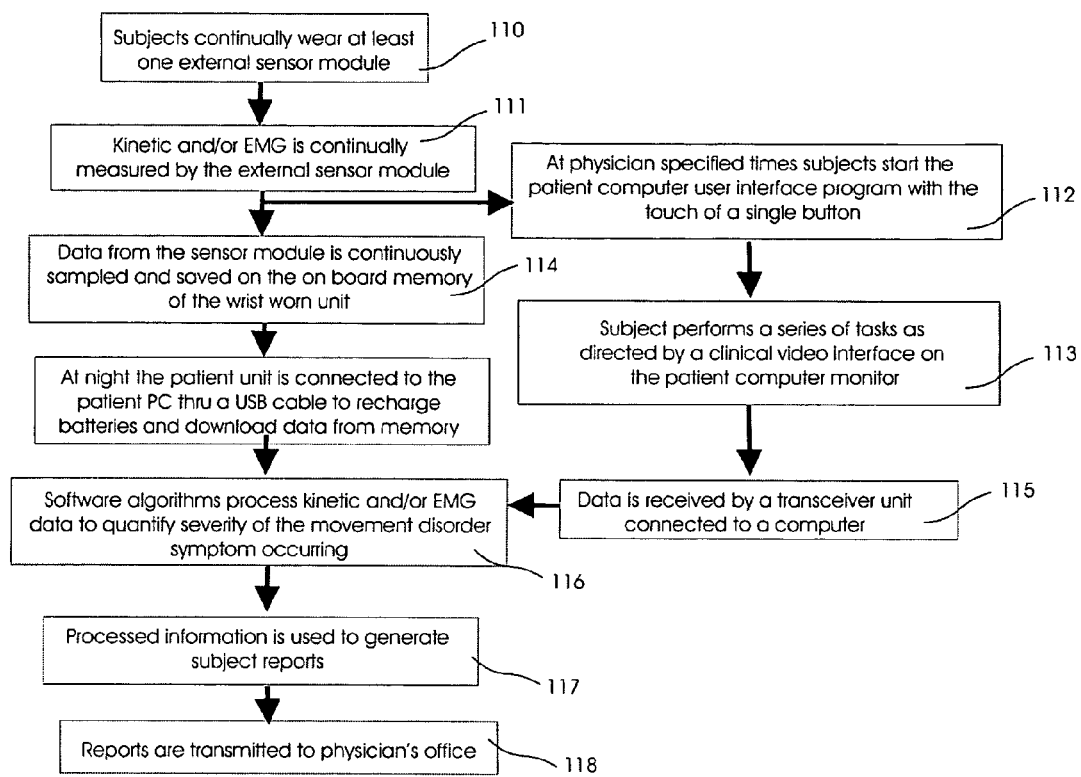
FIG. 10. Flow diagram of system in a combination operating mode.

FIGS. 8-10 show flow diagrams for various operating modes of the system of the present invention. These operating modes should be viewed as examples but not limitations to the present invention and understood that these are but a few of the methods of using the system of the present invention. FIG. 8 is a flow diagram for a continuous operating mode or method for the system of the present invention. In this embodiment, the subjects continually wear at least one external sensor module 80. The external sensor module, which can measure kinetic motion and/or EMG is continually measured by the external sensor module 82. Data from the external sensor module is continuously sampled and stored to memory within a subject worn transceiver module 84. During battery recharging of the device when the patient is not wearing the patient components, the patient components are connected through a hardwire USB link to the patient PC. The stored data is then either transmitted via an RF link to a transceiver unit connected to a computer 86 or transferred through the USB port to the computer. Software algorithms in the computer process kinetic and/or EMG data to quantify the severity of the movement disorder symptom occurring 87. The processed information is then used to generate subject reports or data 88, and the reports or data are transmitted to technician, clinician or physician for review 89.

FIG. 9 is a flow diagram for a task operating mode or method for the system of the present invention. In this mode the subjects intermittently wear at least one external sensor module at technician, clinician or physician prescribed times 100. The subjects may start the patient computer user interface program, preferably with the touch of a single button. The computer transceiver "wakes up" the subject worn transceiver module 102 or the clinical video on the patient computer instructs the subject to press a button on the transceiver module to manually "wake up" the unit. The subject performs a series of tasks as directed by a clinical video, which preferably is viewed on the patient's computer monitor 103. The data from the external sensor module is then sampled and transmitted by radio frequency with the subject worn transceiver module during the tasks 104. The data is received by a transceiver unit connected to the computer 105. The data transmission lasts approximately or only as long as the same time as a programmed collection interval, the subject worn transceiver unit then enters into a "sleep state" 106. Software algorithms in a computer connected to the computer transceiver unit process the kinetic motion and/or EMG data to quantify severity of the movement disorder symptom occurring 107. The processed information is then used to generate subject reports or data 108, and the reports or data are transmitted to technician, clinician or physician for review 109.

FIG. 10 is a flow diagram for a combination operating mode or method for the system of the present invention. In this mode, the subject continually wears at least one external sensor module 110. The external sensor module, which can measure kinetic motion and/or EMG is continually measured by the external sensor module 111. Data from the external sensor module is continuously sampled and stored to memory on the subject worn transceiver module 114. This data is then downloaded to the patient computer at a later time. Software algorithms in the computer process kinetic and/or EMG data to quantify the severity of the movement disorder symptom occurring 116. The processed information is then used to generate subject reports or data 117, and the reports or data are transmitted to technician, clinician or physician for review 118. This method, however, varies from the method described in FIG. 8 in that at technician, clinician, physician or computer at randomly specified times alerts the subject start or has computer starts a video 112, and alerts the subject to perform a series of tasks as directed by the clinical video, which is preferably on the patient's computer monitor 113. During these tasks, data is transmitted by the user worn receiver module and is received by a transceiver unit connected to a computer 115. Software algorithms in the computer process kinetic and/or EMG data to quantify the severity of the movement disorder symptom occurring 116. The processed information is then used to generate subject reports or data 117, and the reports or data are transmitted to technician, clinician or physician for review 118.

The portable movement disorder device of the present invention for measuring the severity of a subject's movement disorder can be worn in any way likely to provide good data on a subject's movement disorder. Examples would include but are not limited to the use of the device on the subject's hand and/or arm; legs, and/or head. Preferably, the movement disorder device is on the arm and/or hand of the subject. FIGS. 6 and 7 and show a schematic of a movement disorder device on a subject's lower arm and hand. In this embodiment, the subject's kinetic motion is measured by a kinetic sensor board (also known as external sensor module) 50. The external sensor module 50 is held firmly to the subject's finger 51 by a velcro strap 52. The external sensor module 50 is connected to a subject worn transceiver module 64 via electrical pathways or wires 54. Optionally, the device may also have at least one EMG electrodes (not shown).

Preferably, the subject worn transceiver module in this embodiment is reasonably small size. Achieving the wrist mount design of this embodiment require the size of the radio used for the device be greatly reduced. Preferably, a commercially available chip (blue tooth technology) is used that can transmit up to 200 ft. Not only will this greatly reduce the size of the device, but the transceiver capability will allow two-way communications between the patient worn unit and the computer unit.

The two-way capability in this particular embodiment will provide multiple benefits. First, by having two-way communications, the unit will be capable of utilizing a protocol where data packets can be resent if corrupted during transmission. Another benefit is that several patient worn units could potentially communicate with a single base station clinician PC. In this scenario, the subject units occupy dedicated time slots to transmit their information. Several subject worn units could operate with a single computer base station in a hospital or home setting. Additionally, multiple units may be worn on a subject to monitor tremor in both hands at the same time. A final benefit of the two-way protocol is that configuration information can be sent to the patient unit over the radio link including power level, frequency, and shut down modes. Shut down modes could be of great benefit for this type of system where the clinical PC can command the subject units to power down between tests thus conserving battery life in the patient unit. Essentially, the technician, clinician, or physician will be able to program the system for continuous recording or to record at certain times for specified intervals.

Preferably, the radio design of this specific embodiment is implemented using a highly integrated radio chip (blue tooth technology) which requires very few external components, consumes less power than a discrete radio design, and requires less physical area than a discrete design. More preferably, the radio chip is takes incoming clock and data and produces a Frequency Modulated carrier when configured as a transmitter, and performs the opposite function when configured as a receiver. This high level of integration makes the only component required to interface to the radio section a unit microcontroller.

With few components and high level of integration, the radio section should be easy to manufacture, have low component cost, and have high field reliability. Preferably, the IC or microprocessor has a controllable RF power output levels and by using the two-way protocol described above, the radio link can operate at a level high enough to ensure reliable data transfer while conserving unit power. Finally, the most preferably, the IC or microprocessor can operate anywhere from 300 MHz to 2.4 GHz providing great flexibility when the system is developed to ensure optimum operation. The 2.4 GHz band is the preferable operating band.

Figure 11:
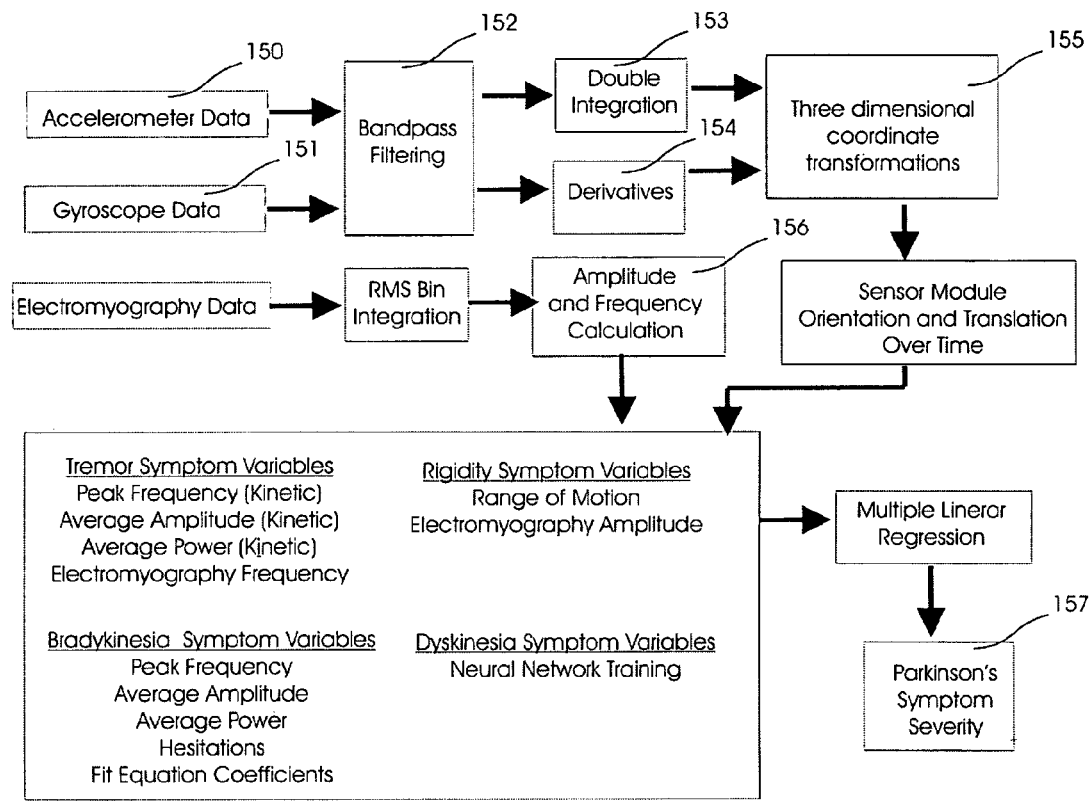
FIG. 11. Flow diagram for one embodiment of the software used in the present invention.

FIG. 11 is a flow diagram for one embodiment of the software used in the present invention. Analog outputs 151, 152 from the accelerometer and gyroscope are converted to linear acceleration and angular velocity with a scaling factor. The linear accelerations and angular velocity inputs are then bandpass filtered 153 to prevent biasing and remove DC drift. The linear acceleration is double integrated to yield linear position. The derivative 154 of the angular velocity is calculated to determine angle. The three dimensional translation and rotation 155 of the module is computed from the information from the three orthogonal accelerometers and three orthogonal gyroscopes. The root mean square (RMS) value of the continuous time EMG signal is calculated over discrete time windows. The amplitude and frequency 156 of the processed EMG signal is calculated. Specific variables are then computed for each Parkinson's symptom based on the processed kinetic and EMG data. Tremor symptom variables may include but are not limited to the peak frequency of the kinetic sensors, the average amplitude of the kinetic sensors, the average power of the kinetic sensors, and the frequency of the EMG signals. Bradykinesia symptom variables may include but are not limited to the peak frequency of EMG or kinetic data, the average amplitude of the kinetic sensors, the average power of the EMG or kinetic sensors, the number of hesitations that occur in a subjects movement, or the linear or exponential fit coefficients used to fit a model to the amplitude of a subject's movement over time. Rigidity symptom variables may include but are not limited to range of motion and EMG amplitude. Dyskinesia symptom variables may include but are not limited to the output of a neural network trained to recognize dyskinesia from other movements using the kinetic sensor data as inputs. The value of each symptom variable for a particular symptom is used in an algorithm that may include but are not limited to multiple linear regression models or neural networks to fit the symptom variables to the qualitative clinicians Unified Parkinson's Disease Rating Scale scores for that symptom 157.

The present invention further includes a drug delivery system. The drug delivery system utilizes in part the input from the external sensors or the scoring of the severity of the subject's movement disorder or the movement disorder symptoms as input into a closed loop control system to deliver medication to lessen or relieve the symptoms of the disorder, or to appropriately treat the disorder in a non-symptomatic way. The drug delivery system comprises the at least one external sensor having a signal for measuring a subject's external body motion or a physiological signal associated with a movement disorder. The drug delivery system comprises at least one external sensor being described earlier in the application. The drug delivery system further comprises a reservoir for some form of medication, preferably liquid, that can either be delivered to the subject internally or transcutaneously. The system further comprises an actuator which when activated and deactivated allows the medication to be delivered from the reservoir to the subject. Finally, the system further comprises a closed-loop control system which activates and deactivates the actuator based in part on a signal from the at least one external sensor.

Figure 12:
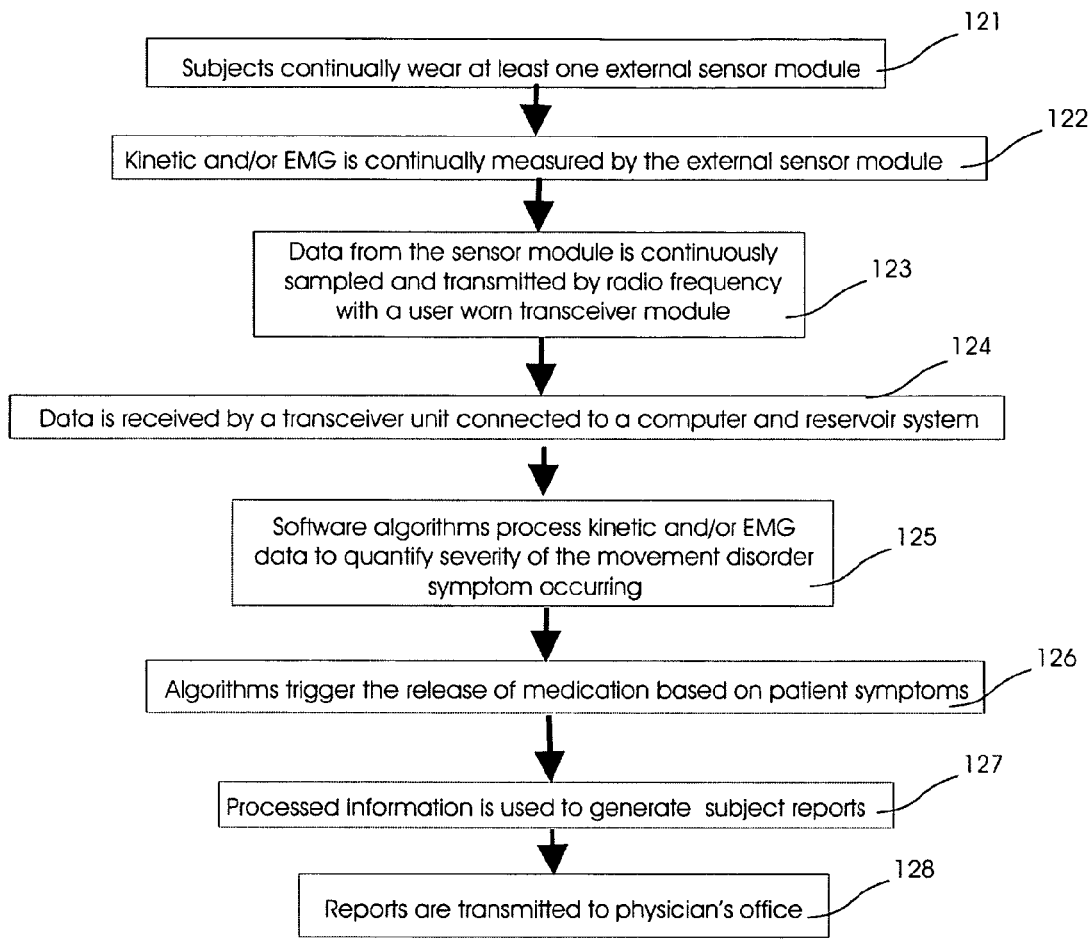
FIG. 12. Flow diagram for one embodiment of a closed-loop drug delivery system of the present invention.

FIG. 12 is a flow diagram for one embodiment of a closed-loop drug delivery system of the present invention. In this embodiment, the subjects continually wear at least one external sensor module 121. Kinetic motion and/or EMG is continually measured by the external sensor module 122. Data from the external sensor module is continuously sampled and transmitted by radio frequency with a subject worn transceiver module 123. The transmitted data is received by a transceiver unit connected to a reservoir system 124 with embedded processing. Software algorithms process kinetic and/or EMG data to quantify the severity of the movement disorder symptom occurring 124. The software algorithms trigger the release of medication based on the subject's symptoms 126, or the overall severity of the movement disorder 125. The processed information is then used to generate subject reports or data 127, and the reports or data are transmitted to technician, clinician or physician for review 128.

Figure 13:
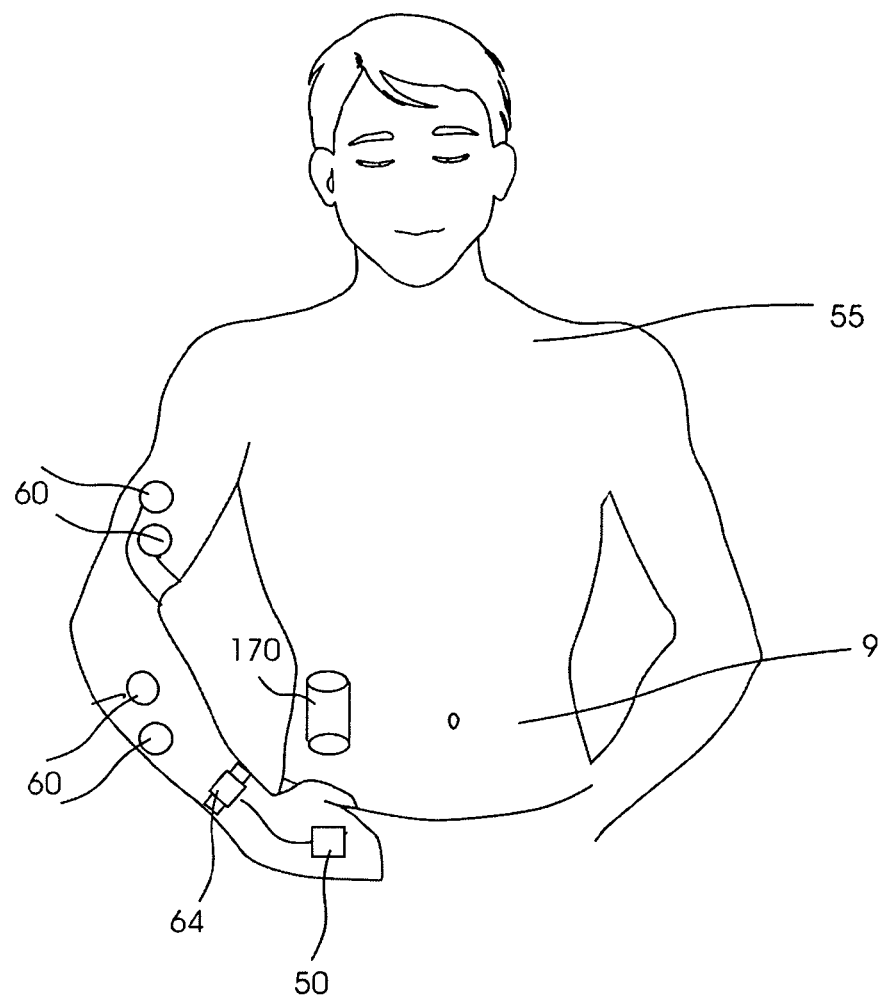
FIG. 13. Schematic showing placement of various components of closed loop drug delivery system with an implantable reservoir.

FIG. 13 is a schematic diagram showing placement of various components of closed loop drug delivery system with an implantable reservoir. In FIG. 13, the subject 55 is wearing a closed loop drug delivery system. The closed loop drug may have an external sensor module 50, a subject worn transceiver module 64, EMG electrodes 60, a reservoir 170 for holding medication with an embedded transceiver and processor and actuator for allowing delivery (not shown), and a controller for activating and deactiving the actuator based in part on the signal from the at least one of the sensor modules 50. In this example a reservoir 170 being implanted into the abdomen 9 of the subject. The reservoir 170 containing medication, which is released into the subject's body through activation of an actuator. The respective transceiver module 64 being connected to the EMG electrodes 60 and external sensor modules 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 170.

Figure 14:
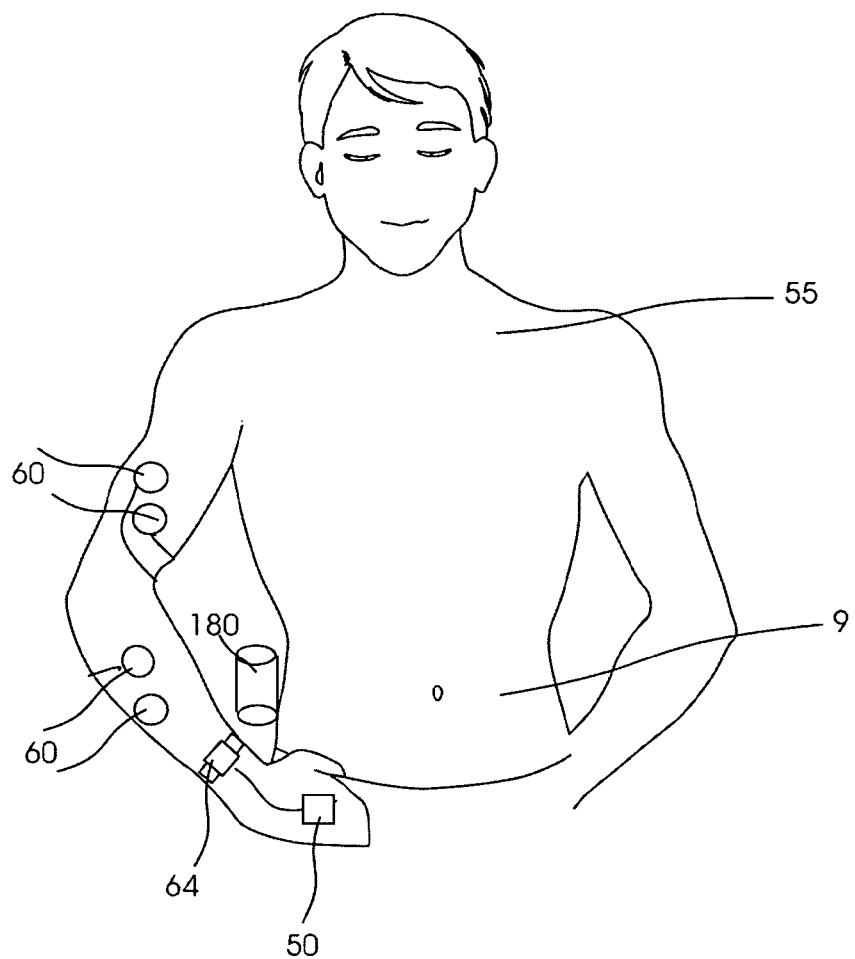
FIG. 14. Schematic showing placement of various components of closed loop drug delivery system with an external reservoir to transcutaneous delivery.

FIG. 14 is a schematic diagram showing placement of various components of a closed loop drug delivery system with an external reservoir to transcutaneous delivery. In FIG. 14, the subject 55 is wearing a closed loop drug delivery system. The closed loop drug delivery system may have an external sensor module 50, a subject worn transceiver module 64, EMG electrodes 60, a reservoir 180 for holding medication with an embedded transceiver and processor and actuator for allowing delivery (not shown), and a controller for activating and deactivating the actuator based in part on the signal from the at least one of the sensor modules 50. In this example a reservoir 180 is attached externally to the abdomen 9 of the subject. The reservoir 180 containing medication, which is released into the subject's body through activation of an actuator. The respective transceiver module 64 being connected to the EMG electrodes 60 and external sensor module 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 180.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A movement disorder device or system for measuring, quantifying and treating a subject's Parkinson's disease based on a calculated severity of symptoms comprising one or more of tremor; bradykinesia, rigidity, or dyskinesia, the device or system comprising:

at least one external sensor having a first signal for measuring a subject's external body motion or physiological signal associated with such external body motion;

an actuator for adjusting a drug or medication for a treatment of the subject's Parkinson's disease or symptoms of Parkinson's disease; and a processor for receiving the first signal and calculating the quantified severity of the subject's symptoms of tremor, bradykinesia, rigidity, or dyskinesia in real time and transmitting a second signal to activate the actuator to release the drug or medication based in part on the calculated quantified severity of at least one symptom of Parkinson's disease.

2. The movement disorder device or system in claim 1, further comprising a reservoir for the drug or medication, and from which the drug or medication is released based in part on the calculated quantified severity of at least one symptom of Parkinson's disease.

3. The movement disorder device or system in claim 2, further comprising a transceiver for receiving the first and/or second signal, and a controller or the processor for controlling the release of the drug or medication based in part on the calculated quantified severity of at least one symptom of Parkinson's disease.

4. The movement disorder device or system in claim 3, wherein the controller or processor are part of a closed loop delivery system.

5. The movement disorder device or system in claim 2, wherein the first and/or second signal are transmitted to a remote communication station for display and review by a physician, clinician, technician or monitoring service to review the severity of the subject's symptoms and, if necessary, modify the subject's treatment protocol.

6. The movement disorder device or system in claim 5, wherein the reservoir further comprises a controller to which a third signal can be sent from the remote communication station to modify the subject's treatment protocol.

7. The movement disorder device or system in claim 5, further comprising a monitor for the subject wherein instructions from the physician, clinician, technician or monitoring service can be sent through the remote communication station and be displayed to the subject on the monitor.

8. A movement disorder device or system for measuring, quantifying and treating a subject's Parkinson's disease based on a calculated severity of symptoms comprising one or more of tremor, bradykinesia, rigidity, or dyskinesia, the device or system comprising:
at least one external sensor having a signal for measuring a subject's external body motion or physiological signal associated with such external body motion; and
a processor for receiving the signal and calculating the quantified severity of the subject's symptoms of tremor, bradykinesia, rigidity, or dyskinesia in real time
wherein the calculated quantified severity of the subject's symptoms of tremor, bradykinesia, rigidity or dyskinesia is used to treat the subject's Parkinson's disease or symptoms of Parkinson's disease using a drug or medication.

9. The movement, disorder device or system in claim 8, further comprising a closed loop control system wherein the pharmaceutical is in a reservoir with an actuator which is controlled in part by a closed loop control system.

10. The movement disorder device or system in claim 8, wherein the severity of the subject's Parkinson's disease or symptoms of Parkinson's disease is calculated in less than 30 seconds.

11. The movement disorder device or system in claim 8, wherein the device or system is used by a physician, veterinarian, technician or clinician for analysis or evaluation of the subject's movement disorder, for pharmaceutical research, or for delivery of pharmaceutical compounds.

12. The movement disorder device or system in claim 11, further comprising a remote communication station which receives and displays the signal associated with the subject's external body motion or the calculated quantified severity of the subject's symptoms for analysis or evaluation by the physician, veterinarian, technician or clinician.

13. The movement disorder device or system in claim 8, wherein the calculated quantified severity of the subject's symptoms of tremor, bradykinesia, rigidity, or dyskinesia is further used to generate subject reports or data and the reports or data are transmitted to a technician, veterinarian, clinician or physician for review.

14. The movement disorder device or system in claim 11, wherein the signal associated with the subject's external body motion or the calculated quantified severity of the subject's symptoms is used to modify the subject's pharmaceutical treatment protocol.

15. A method of measuring, quantifying and treating a subject's Parkinson's disease based on a calculated severity of symptoms comprising one or more of tremor, bradykinesia, rigidity, or dyskinesia, the method comprising the steps of:
measuring with a first device the external body motion of a subject on a drug or medication treatment protocol in order to determine a severity of the subject's Parkinson's disease or symptoms of Parkinson's disease;
transmitting a radio frequency signal from the first device worn by a subject based in part on the subject's measured external body motion to a remote communication system for review by a physician, clinician, technician or remote monitoring service;
scoring the severity of a subject's symptoms of tremor, bradykinesia, rigidity, or dyskinesia with a processor either before or after transmitting the radio frequency signal to provide a quantification of the severity of the symptoms based in part on the measured external body motion; and
modifying the subject's drug or medication treatment protocol in part on the severity of the measured symptoms.

16. The method of claim 15, wherein the radio frequency transmitted signal is used to generate subject reports or data.

17. The method of claim 15, wherein the scoring of the severity of a subject's tremor, bradykinesia, rigidity, or dyskinesia is done in real time.

18. The method of claim 15, wherein the first device uses at least one accelerometer and at least one gyroscope to measure external body motion in order to determine a severity of the subject's Parkinson's disease or symptoms of Parkinson's disease.

19. The method of claim 15, wherein the first device alerts the subject to begin to perform a series of tasks during which external body motion is measured in order to determine a severity of the subject's Parkinson's disease or symptoms of Parkinson's disease.

20. The method of measuring severity of a subject's movement disorder in claim 15, wherein the transmitted signal is sent via internet, cell towers, land phone lines or cable to the remote communication station.

* * * * *